(12) United States Patent
Smith et al.

(10) Patent No.: US 8,409,090 B2
(45) Date of Patent: *Apr. 2, 2013

(54) TISSUE RETRACTOR AND METHOD FOR USING THE RETRACTOR

(75) Inventors: Kevin W. Smith, Coral Gables, FL (US); Matthew A. Palmer, Miami, FL (US); Juergen Kortenbach, Miami Springs, FL (US); Jose Francese, Miami Springs, FL (US)

(73) Assignee: ID, LLC, Miami, FL (US)

( * ) Notice: Subject to any disclaimer, the term of this patent is extended or adjusted under 35 U.S.C. 154(b) by 215 days.

This patent is subject to a terminal disclaimer.

(21) Appl. No.: 12/767,328

(22) Filed: Apr. 26, 2010
(Under 37 CFR 1.47)

(65) Prior Publication Data

US 2011/0071360 A1  Mar. 24, 2011

Related U.S. Application Data

(62) Division of application No. 10/728,389, filed on Dec. 5, 2003, now Pat. No. 7,731,655.

(51) Int. Cl.
*A61B 1/32* (2006.01)
(52) U.S. Cl. .......................... 600/217; 600/206
(58) Field of Classification Search .......... 606/41, 606/119, 139, 144, 148; 600/217, 374, 206; 607/128
See application file for complete search history.

(56) References Cited

U.S. PATENT DOCUMENTS

| | | | | |
|---|---|---|---|---|
| 4,103,690 A * | 8/1978 | Harris | ............. | 607/128 |
| 5,237,996 A * | 8/1993 | Waldman et al. | ............. | 600/374 |
| 5,282,845 A * | 2/1994 | Bush et al. | ............. | 607/128 |
| 5,492,119 A * | 2/1996 | Abrams | ............. | 607/128 |
| 6,623,481 B1 * | 9/2003 | Garbagnati et al. | ............. | 606/41 |

* cited by examiner

*Primary Examiner* — Julian Woo
(74) *Attorney, Agent, or Firm* — Mayback & Hoffman, P.A.; Gregory L. Mayback

(57) ABSTRACT

A retractor for manipulating an object includes a body having proximal and distal ends and a retraction device with a head connected to the distal end of the body, a connector movably disposed in the body, and flexible needles of a shape memory material having a memory shape. The needles are connected to the connector and each have a distal tip. The memory shape of the needles include a portion with an arcuate shape biasing the needles in a memory direction out and away from the head and toward the body to position the distal tip of each of the needles closer to the body when the needles are fully extended out of the head than when the needles are only partially extended out of the head. An actuation device is connected to the proximal end of the body and operatively connected to the connector through the body, the actuation device, upon actuation thereof, moves the connector to selectively extend the needles out of the head in different directions and withdraw the needles into the head.

20 Claims, 40 Drawing Sheets

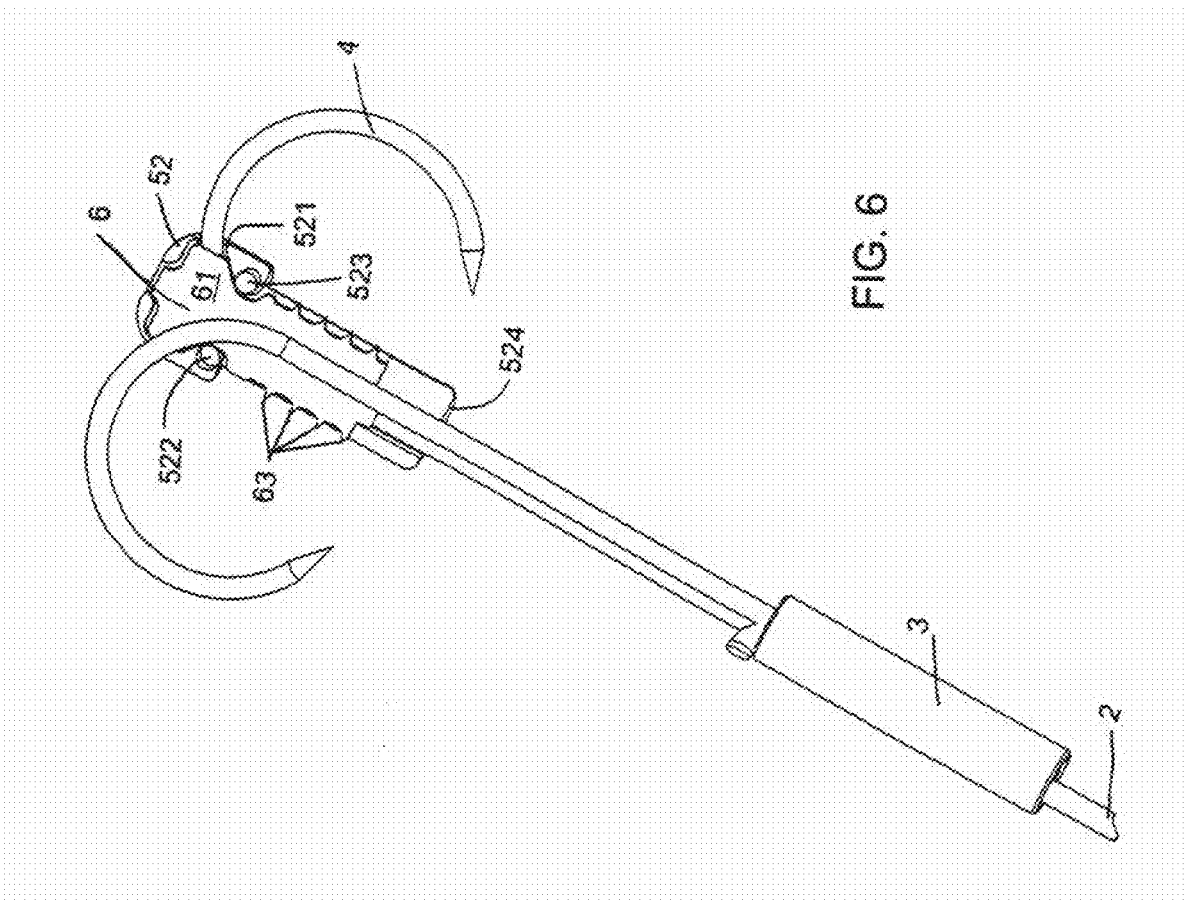

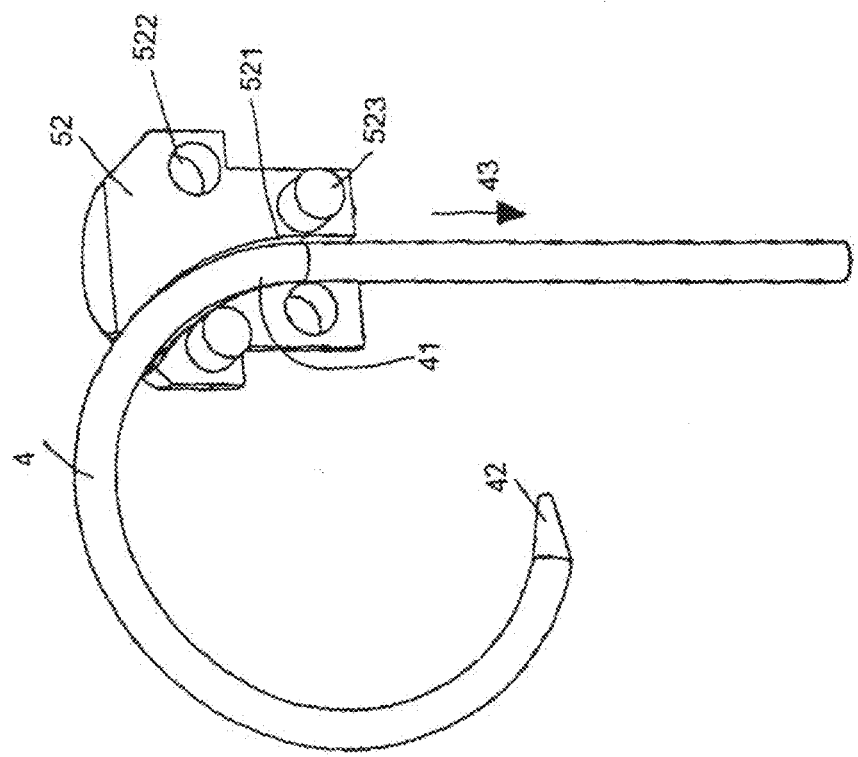

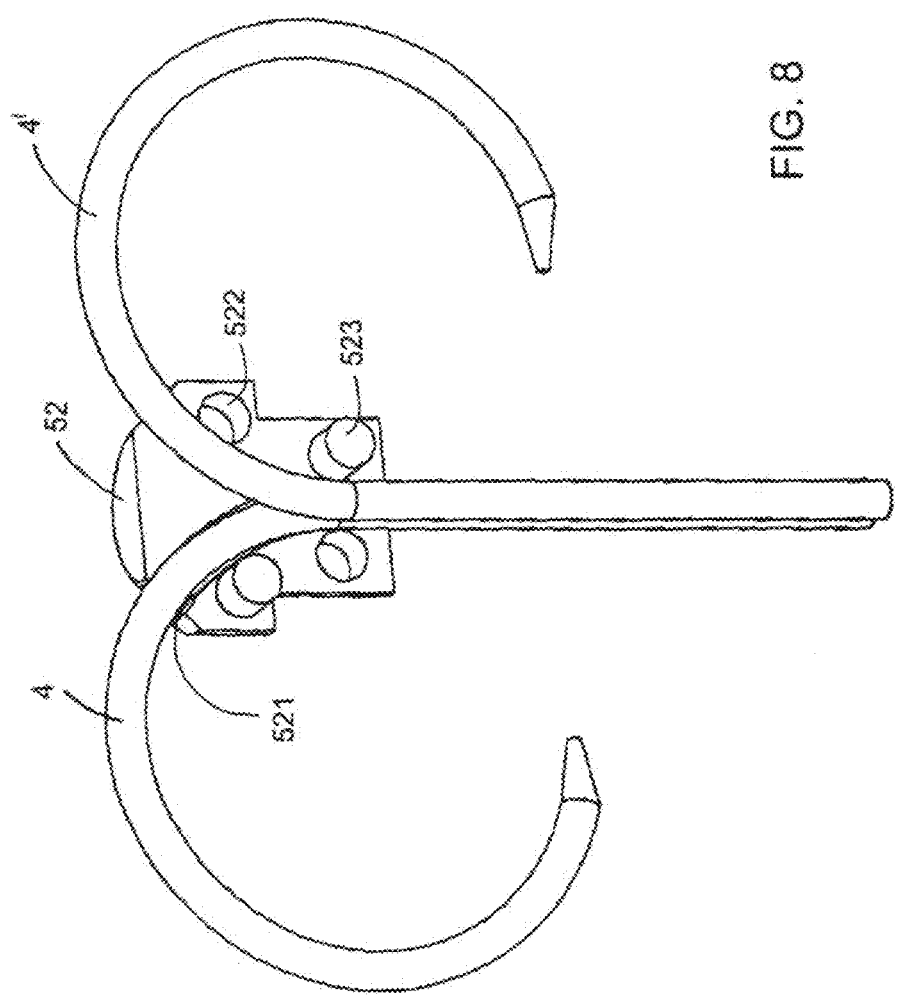

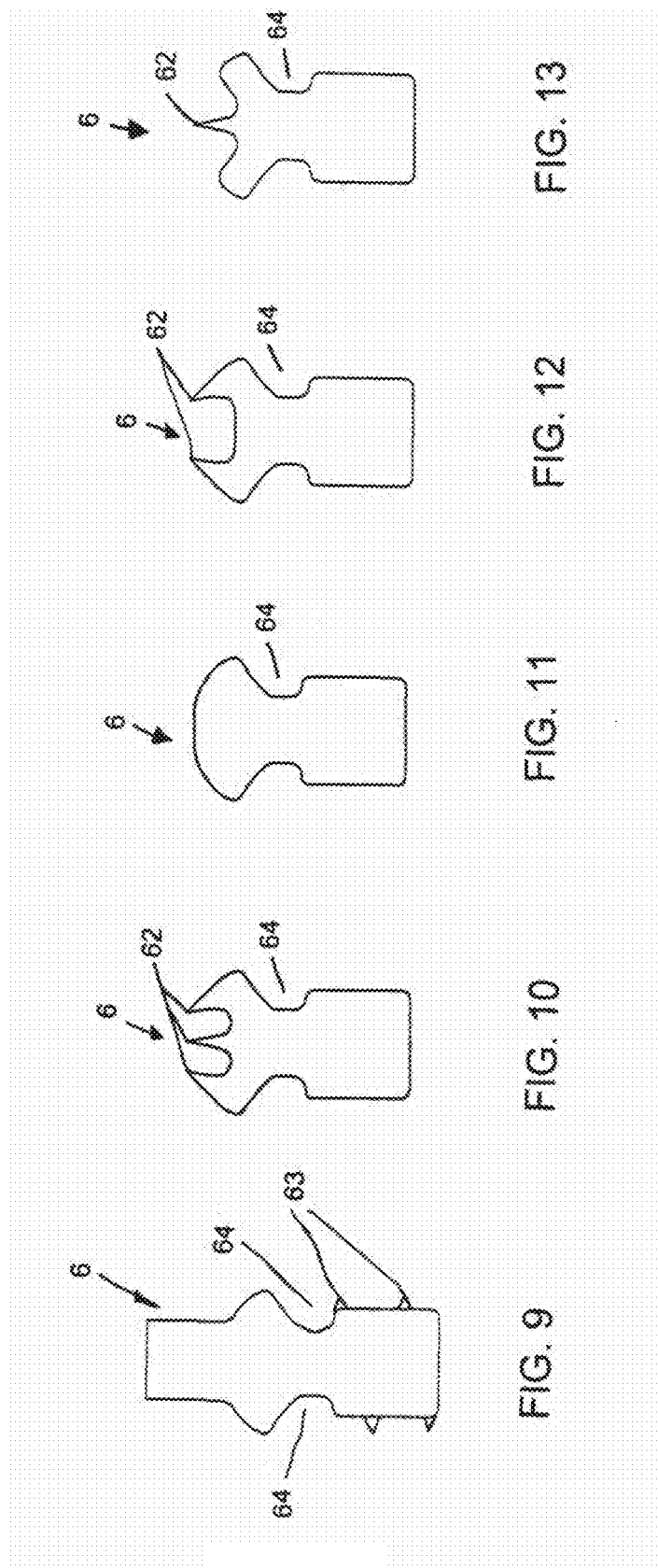

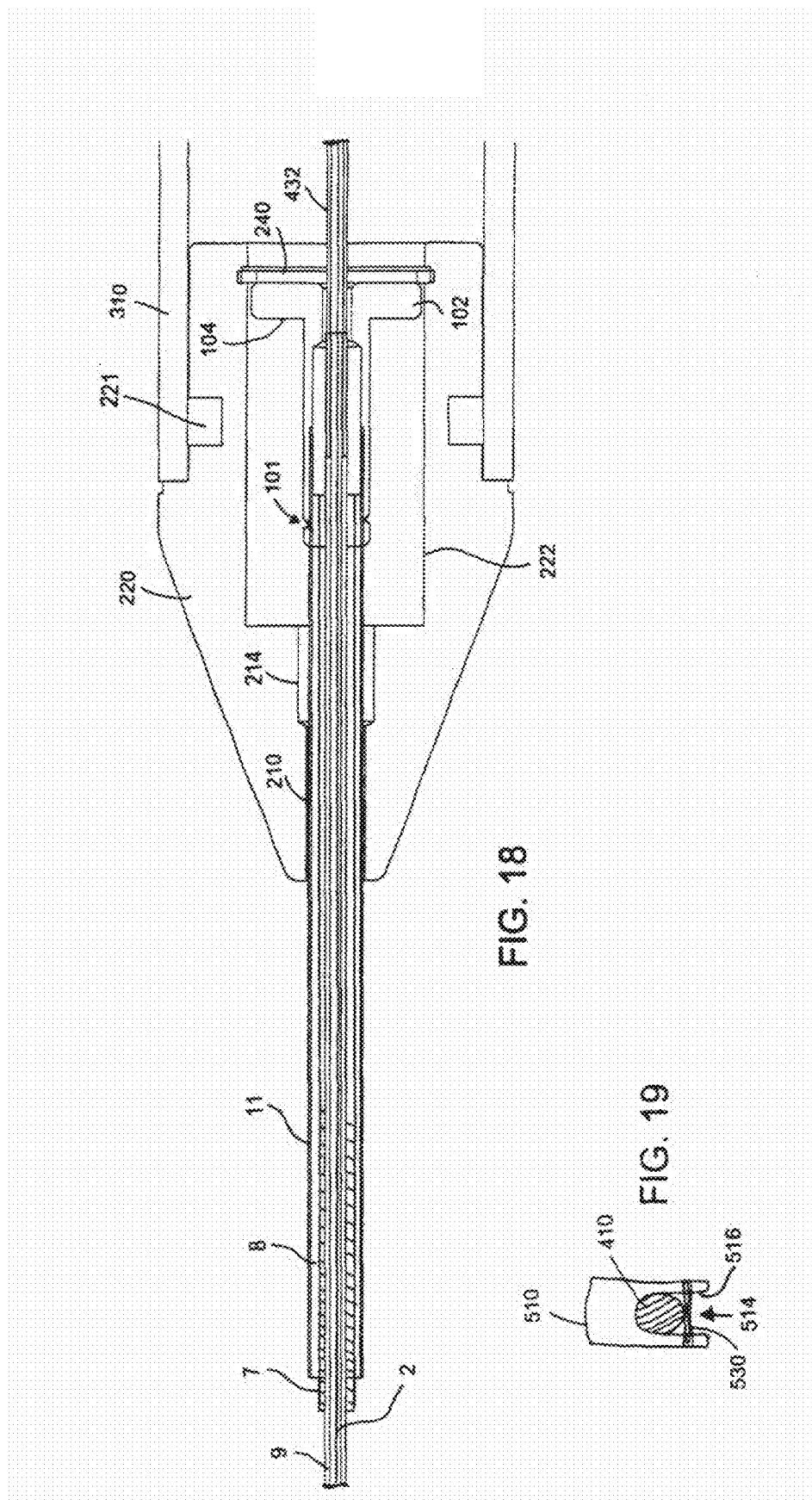

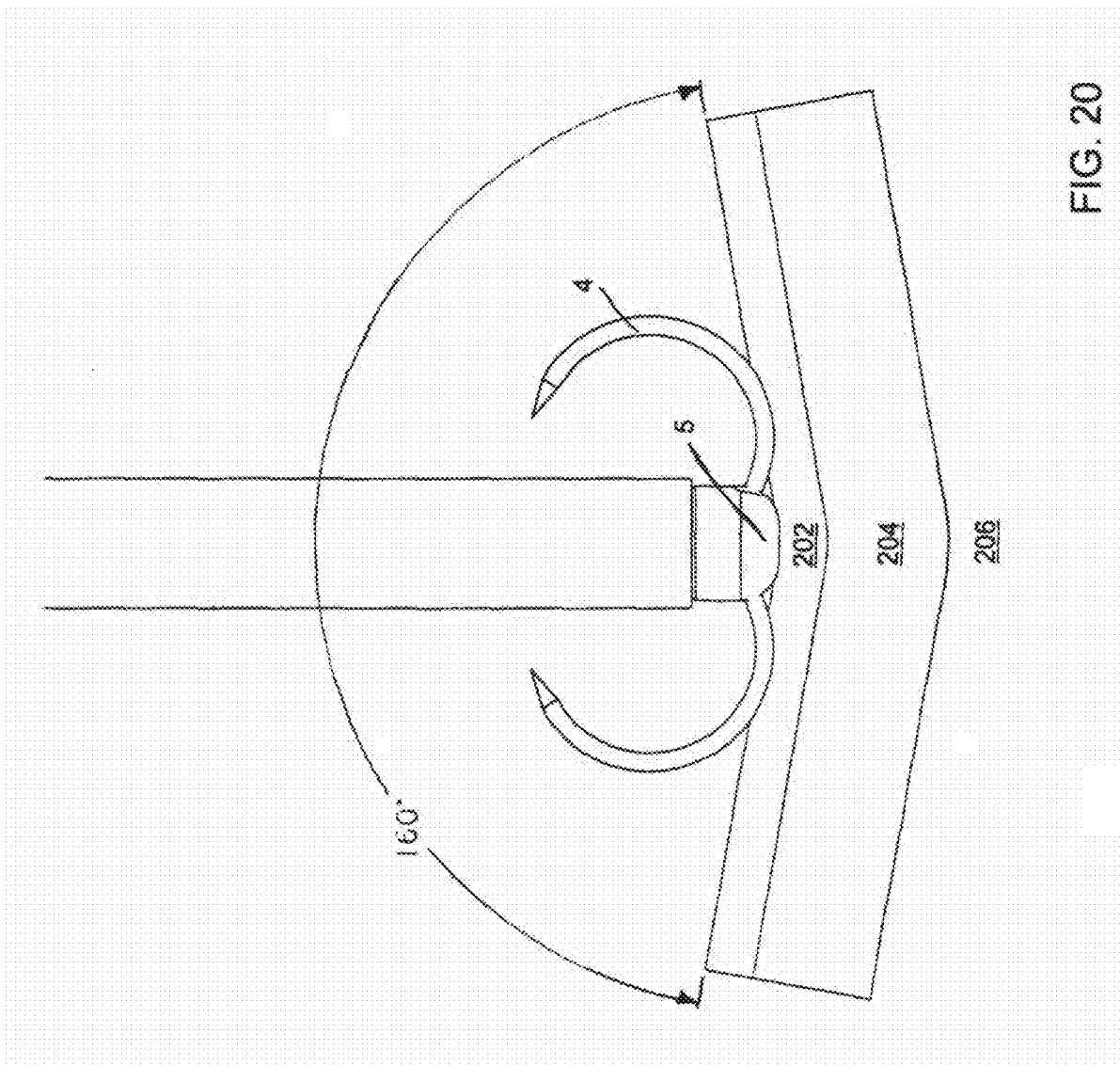

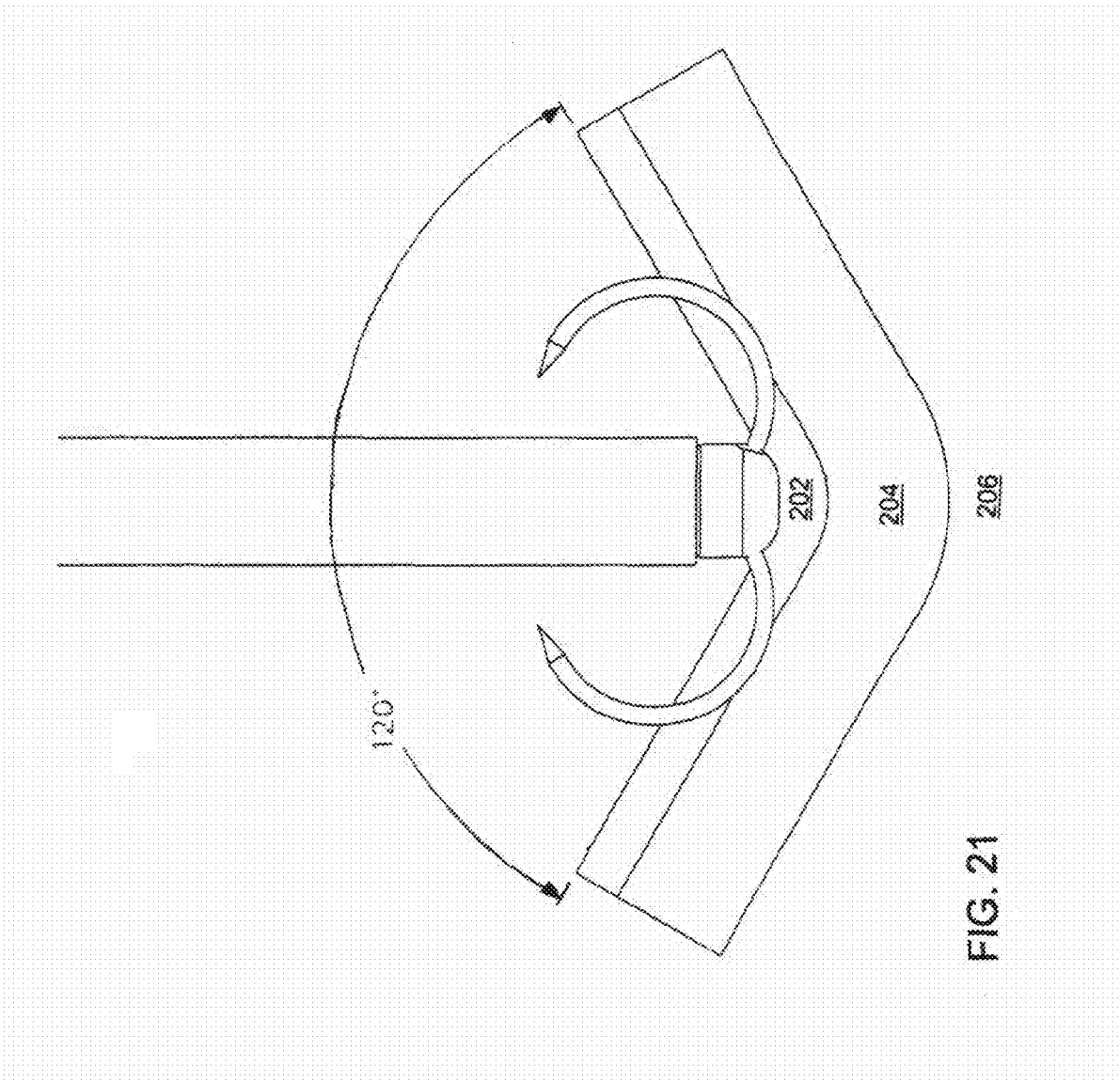

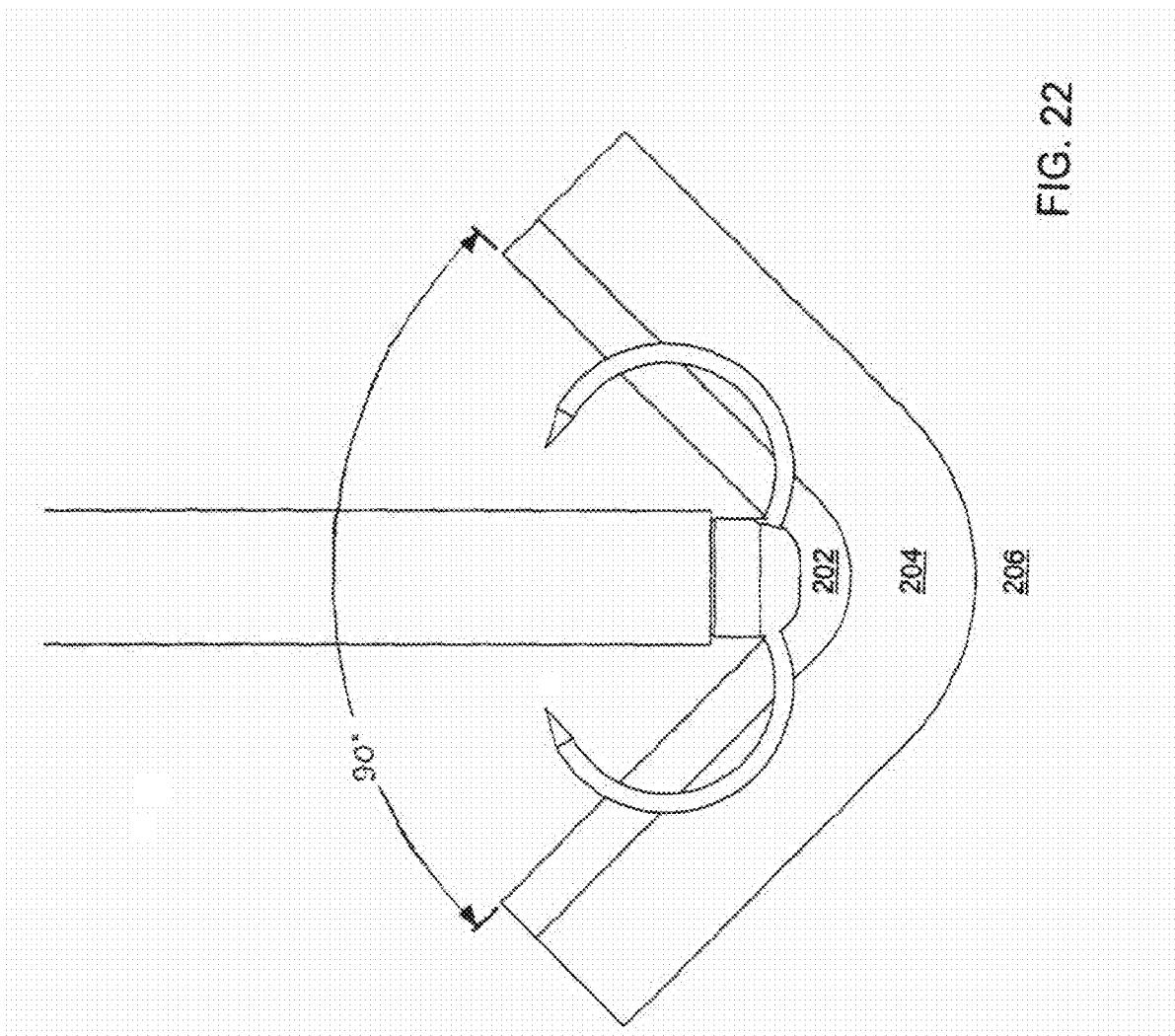

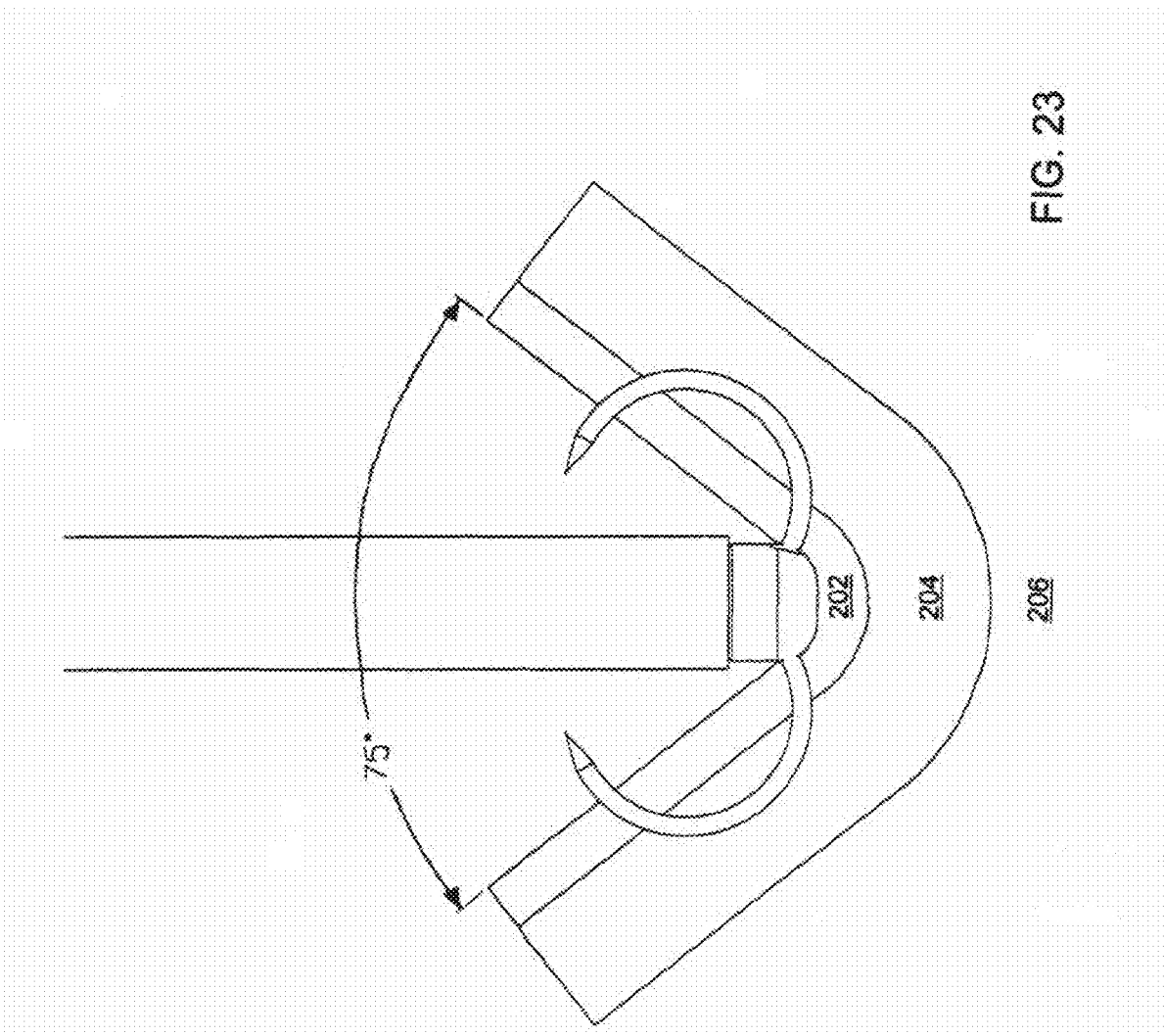

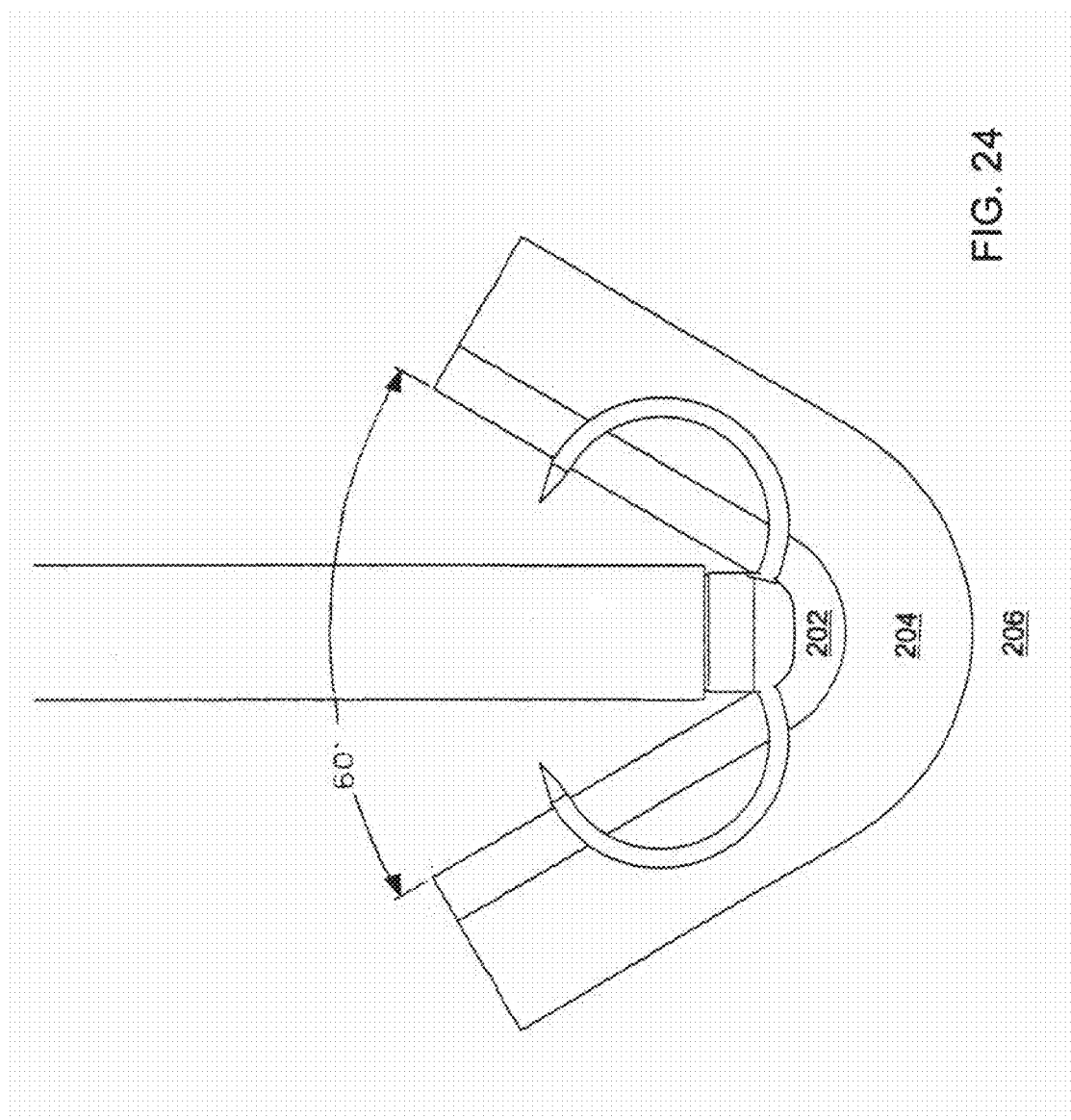

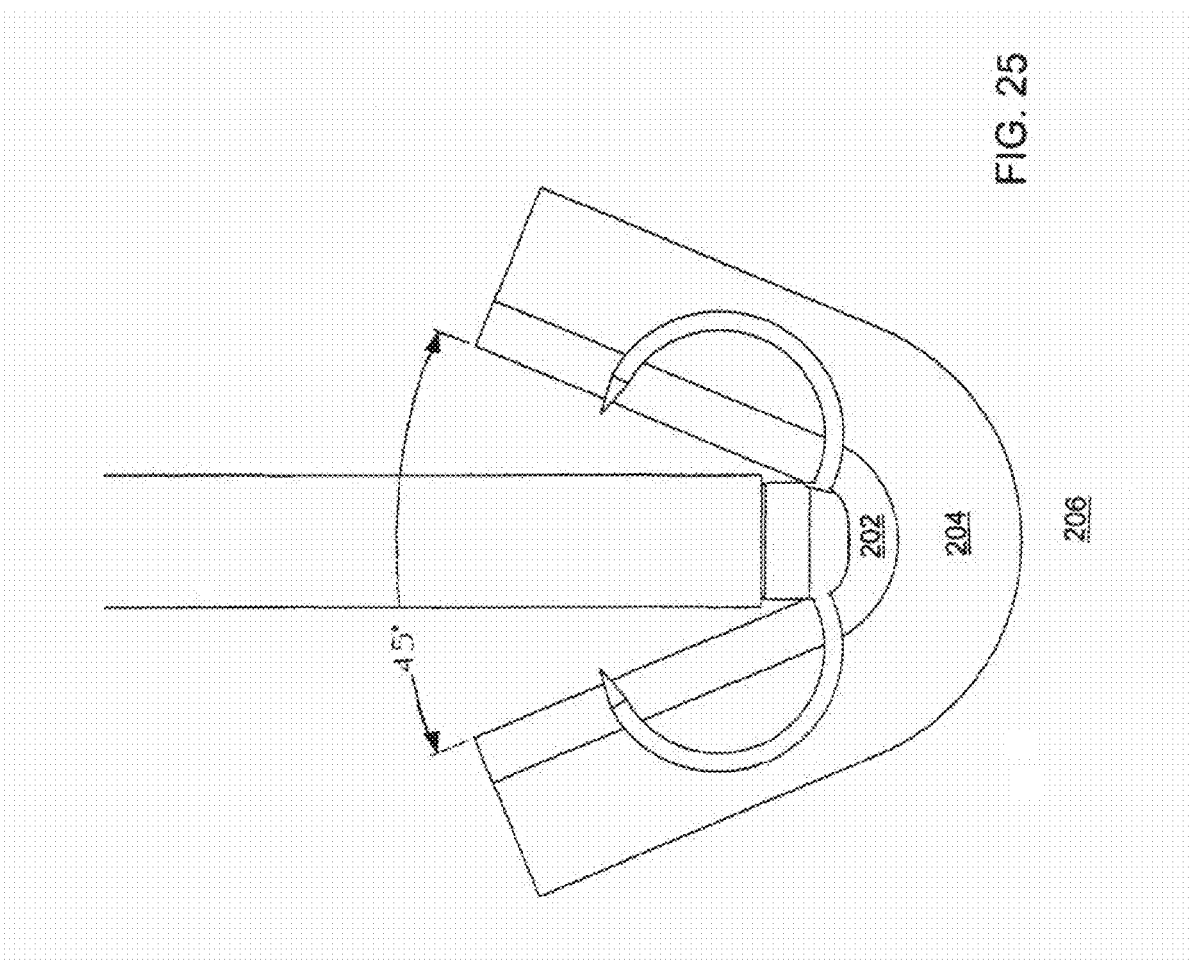

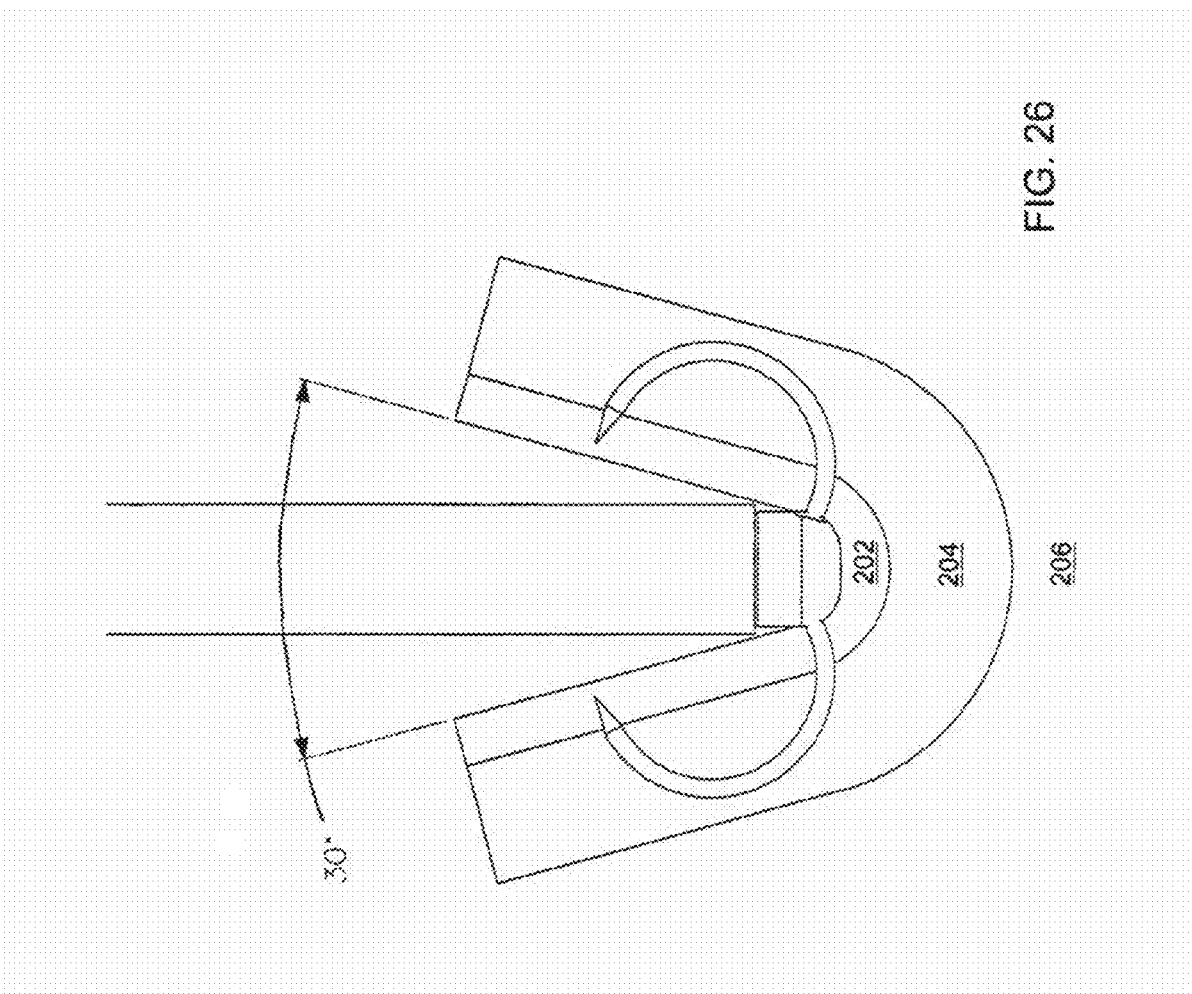

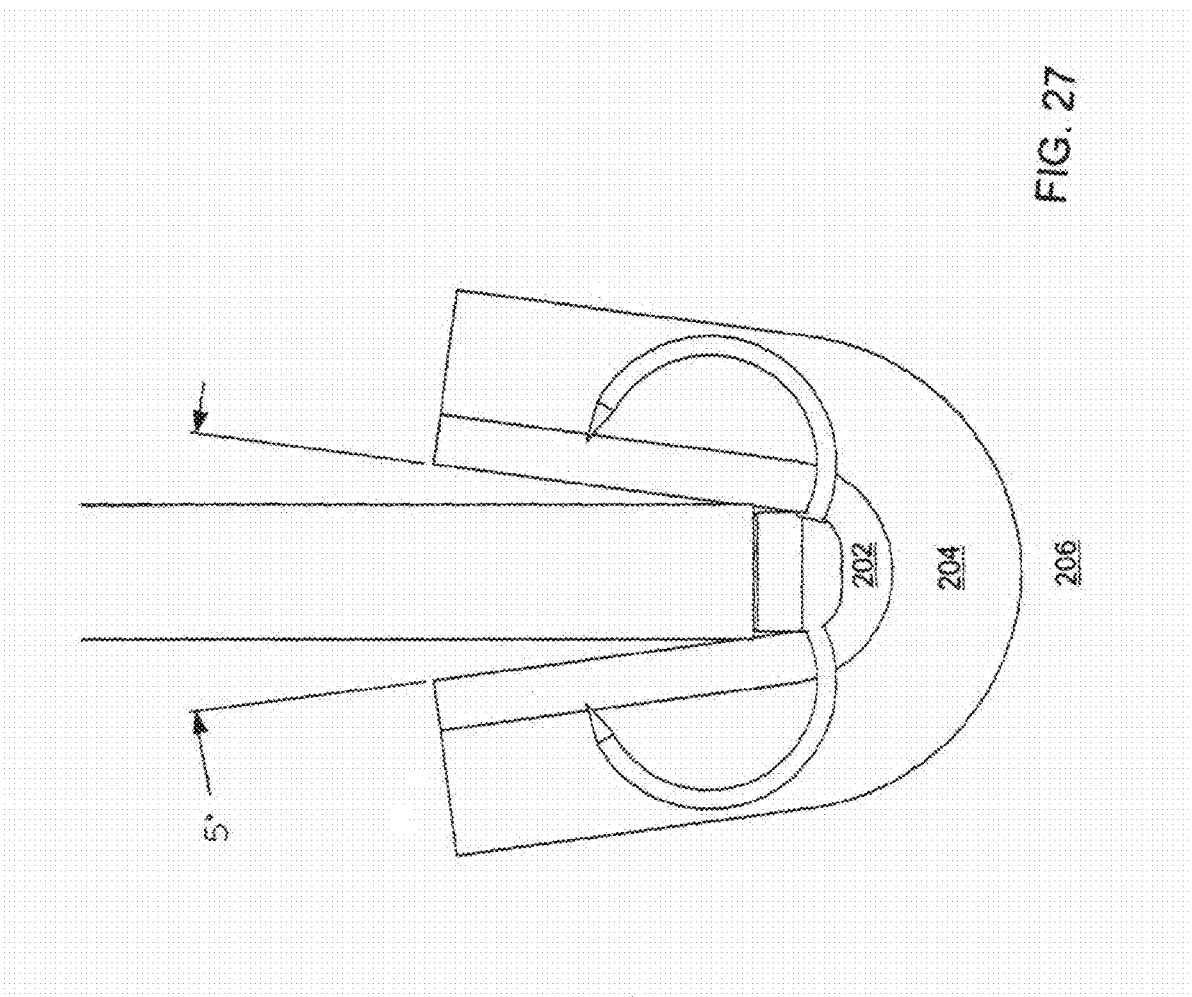

TISSUE RETRACTOR AND METHOD FOR USING THE RETRACTOR

CROSS-REFERENCE TO RELATED APPLICATION

This application is a divisional application of U.S. patent application Ser. No. 10/728,389, filed Dec. 5, 2003, now U.S. Pat. No. 7,731,655, the prior application is herewith incorporated by reference in its entirety.

BACKGROUND OF THE INVENTION

1. Field of the Invention

The present invention relates to a tissue retractor, especially a flexible tissue retractor used as an endoscopic device that is passed through a working channel of a flexible endoscope. The tissue retractor has application in endoscopic and open surgery, including flexible endoscopy, laparoscopy, and general surgery. It can be made rigid or flexible and in lengths and diameters to suit the requirements of the surgical field. The flexible endoscopic tissue retractor is used to hold gastrointestinal tissue so that it can be retracted or manipulated in some way. The tissue retractor can be configured to allow grasping of specific layers of the gastrointestinal wall by adjusting the shape and/or length of the needles and their exit points at the tip of the device. For example it can be configured to grasp through the mucosal layer, and into the muscular layer, thus providing a more secure connection to the tissue and allowing manipulation of the entire thickness of the tissue. Alternately, it can be configured to grasp the mucosal layer allowing manipulation of the mucosal layer only.

2. Description of Related Prior Art

A number of conventional devices exist in the prior art, which devices are used to manipulate the tissue during the endoscopic surgical procedure for treatment of Gastroesophageal Reflux Disease (GERD).

For example, U.S. Pat. No. 6,494,888 B1 to Laufer et al. (referred to hereinafter as "Laufer") describes an instrument for reconfiguring stomach tissue. A tissue manipulator 700 includes an elongated cable assembly 716 and a distal end effector 718 actuated by the cable assembly 716 to perform various steps in the tissue reconfiguring procedure. See Laufer at FIGS. 9A to 9F. The end effector 718 has two jaw members 720, 722 that engage tissue, in particular, tissue at the gastroesophageal junction (GEJ). During the process of implanting the two-part fastener 732, 734 (see Laufer at FIG. 8), a coil 740 is rotated into the GEJ tissue and, after being screwed therein to a sufficient extent, is used to pull the GEJ tissue between the opening defined by the two jaw members 720, 722 in an open position illustrated, for example, in FIGS. 9D and 9E. The coil tissue puller 740, 741, 742 is shown, in particular, in FIG. 3D. The puller has certain disadvantages, however. The coil 740 can penetrate too far, causing possible negative consequences if the stomach is entirely breached (through the mucosa, muscularis, and serosa layers). Because the aorta, liver, diaphragm and other vital organs are disposed adjacent to the fundus of the stomach, if the coil 740 passes through the serosa, there is a significant chance of damage to the vital organs. Also, upon withdrawal, the coil 740, due to its inherent shape, can become stuck in the tissue and, thereby, cause damage to the tissue when the user must forcefully retract the entire assembly 718. Depending on the angle of entry, it is possible that the coil 740 only enters the mucosa. If this occurs, because the mucosa is a relatively thin, loosely attached layer, there is a high probability that the fastener 732, 734 will be only implanted in the mucosa and, therefore, result in a failed implantation procedure. Also, for fasteners that coil into the tissue, the tissue is compressed disadvantageously because rotation of the coil can twist the tissue as the coil is threaded in, which twisting can damage the tissue and cause it to weaken. Also, to advance the coil into the tissue, the coil must be rotated. It is inherently more difficult to transmit torque through a slender flexible device than it is to transmit thrust loads, thus, pushing the needles into the tissue is a more reliable actuation measure than twisting the coil into the tissue. Also, because the forces applied to the tissue by the engaging point of the device is not accompanied by an opposite reacting force of another engaging point of the device, all reaction forces must be provided through the shaft of the device.

A common general flexible endoscopic tissue grasper is most widely used today for manipulating gastrointestinal tissue (for example, one that is made by the Olympus company under the name Olympus Grasping Forceps (Catalog Number FG-49L-1)). A drawback to the Olympus grasper is its inability to reliably grasp muscularis through the mucosal layer. Another drawback is the requirement to maintain pressure on the handle while grasping the tissue. This ties up the user's hands and could lead to inadvertent release of the tissue.

The prior art devices are not constructed to easily, securely, selectively, and precisely engage the tissue during the surgical procedure.

SUMMARY OF THE INVENTION

As it is well known, the tissue in the alimentary tract has three main layers that are, from the innermost layer to outermost layer, the mucosa, the muscularis, and the serosa. The mucosa is a relatively thin layer, loosely attached to the muscularis, and retraction of the mucosa only will not provide a sufficient plication for insertion of a fastener for the treatment of GERD. Retraction of entire thickness of the stomach wall is desired, as such retraction will provide a beneficial plication for insertion of a GERD-treating plication fastener. It is not desirable to perforate the serosal layer. One of the most significant reasons is that an unsealed perforation of the serosa, if sufficiently large, could allow leakage of gastric contents into the peritoneal or thoracic cavities causing a potentially fatal infection.

It is accordingly an object of the present invention to provide a tissue retractor and method for using the retractor that overcome the hereinafore-mentioned disadvantages of the heretofore-known devices and methods of this general type and that can effectively grab the tissue of the alimentary tract during operation and avoid reaching into the serosa, and can grab the tissue without compressing and/or tearing the tissue.

Various endoscopic procedures require manipulation of specific layers in the gastric wall. For instance, in the case of mucosal resection, the mucosa is tented away from the muscularis and resected away. Such a procedure is currently performed by injecting fluid beneath the mucosa to, thus, lift the mucosa from the muscularis. The mucosal tissue is, then, resected using electrocautery. The tissue retractor of the present invention can be used to selectively grasp the mucosa and lift it from the muscularis, thus enabling and simplifying mucosal resection. In the case of forming a full thickness plication in the stomach, the stronger muscular layer of the gastric wall must be grasped to ensure that the full thickness of the wall will be retracted when forming the plication. By tailoring the needles and the way in which they exit from the tip of the retractor, the retractor can be made to selectively grasp the different layers in the gastric wall. Being able to grasp a specific layer of the gastrointestinal wall is advantageous depending on the requirements of the specific procedure being performed.

The tissue retractor of the present invention has applications in laparoscopic and general surgery as well. It can be used to retract organs that are in the way of the surgical field, or to appose and hold tissue in place during suturing. An advantage to an organ retractor or tissue apposition device according to the present invention is the ability to retain the tissue without having to clamp onto it. The tissue retractor atraumatically retains the tissue by penetrating it with fine needles. To further reduce the trauma to the tissue, the needles can be formed with a conical point instead of a faceted point. This is especially advantageous when retracting sensitive organs such as the pancreas. Currently available tissue graspers use more aggressive serrated articulating end effectors, which require clamping forces to retain the tissue and, therefore, potentially cause trauma in the process.

A common procedure during flexible endoscopy is the exchange of an endoscope during a procedure. If the first scope is in a position within the alimentary tract that was difficult to achieve, and it is desired that the second (exchange) scope be in the same position, the tissue retractor could be used to guide the second scope into the position of the first scope. A flexible endoscopic version of the retractor according to the present invention can be provided with a removable handle. Therefore, when a scope exchange is necessary, the tissue retractor can be passed through the first scope and deployed in the tissue at the desired location. The handle of the tissue retractor can, then, be removed. The first scope can, then, be slid over the tissue retractor shaft, leaving the retractor shaft in-place, and removed. Then, the second scope can be fed over the tissue retractor shaft, much like a guidewire, and the scope advanced to the original position. Thereafter, the shaft can be released and removed when desired.

Also, a version of the retractor can be made that allows the distal tip of the retractor to be deployed in the tissue and, then, decoupled from the main shaft. In such an embodiment, the distal tip of the device is coupled removably to the shaft and the actuation wire is coupled removably to the needles. The needles are deployed on the target tissue and the shaft of the device is pulled proximally, thus allowing the actuation wire to slip free of the needles and the tip to slide free of the shaft. The released tip being firmly attached to the tissue has application as a marker, suture attachment points for a purse string closure, a tissue apposition suture, and an anchoring point for various things such as pH probes, miniature capsule cameras, and feeding tubes.

The device and method of the present invention allows the needles to be configured such that they can be made to penetrate deep through the mucosa and into the muscularis, making a more secure attachment to the tissue, while substantially reducing the possibility of puncturing the serosa, or penetrate less deep to grasp only the mucosal layer. The present invention engages the tissue at two opposing points, so that the tissue-engaging forces of each point react against the forces of the other; the result is that there is very little reaction load transmitted to the flexible shaft of the device. This deployment of the device does not require substantial torque or thrust loads to be supplied by the shaft. The present invention provides better visibility during placement of the retractor as no jaws are used that could obscure a view of the retraction site. It is also less traumatic to the tissue than a conventional articulating grasper due to the fine diameter and non-cutting points of the needles. The handle can be released from the user's grasp after the needles have been deployed, while still maintaining a secure attachment to the tissue, which frees the user to do other tasks after the tissue has been manipulated or is being manipulated. The tissue retractor is separate from an endoscope but sized to fit within a working channel of the endoscope.

In accordance with certain embodiments, the present invention provides a retractor for manipulating an object, where the retractor includes a body having proximal and distal ends and a retraction device with a head connected to the distal end of the body, a connector movably disposed in the body, and flexible needles of a shape memory material having a memory shape. The needles are connected to the connector and each have a distal tip. The memory shape of the needles include a portion with an arcuate shape biasing the needles in a memory direction out and away from the head and toward the body to position the distal tip of each of the needles closer to the body when the needles are fully extended out of the head than when the needles are only partially extended out of the head. An actuation device is connected to the proximal end of the body and operatively connected to the connector through the body, the actuation device, upon actuation thereof, moves the connector to selectively extend the needles out of the head in different directions and withdraw the needles into the head.

Other features that are considered as characteristic for the invention are set forth in the appended claims.

Although the invention is illustrated and described herein as embodied in a flexible tissue retractor and method for using the retractor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 6 is a fragmentary perspective view of the components of FIG. 4 with a shim and tip half of FIGS. 2 and 3;

FIG. 7 is an enlarged, fragmentary, perspective view of a portion of one of the tip halves of FIGS. 2 and 3 with a needle accommodated therein;

FIG. 8 is an enlarged, fragmentary, perspective view of the portion of the tip half of FIG. 6 with both needles of FIGS. 1 to 5;

FIG. 9 is an elevational view of an alternative embodiment of the shim of FIG. 6;

FIG. 10 is an elevational view of an alternative embodiment of the shim of FIG. 6;

FIG. 11 is an elevational view of an alternative embodiment of the shim of FIG. 6;

FIG. 12 is an elevational view of an alternative embodiment of the shim of FIG. 6;

FIG. 13 is an elevational view of an alternative embodiment of the shim of FIG. 6;

FIG. 18 is a fragmentary, cross-sectional view of an enlarged portion of the distal components of the handle of FIG. 17;

FIG. 19 is a cross-sectional view of a button assembly of the handle of FIG. 14 along section line 19-19;

FIGS. 20 to 27 are fragmentary, partially cross-sectional and partially plan views of the method of using the retractor according to the invention to retract tissue at different retraction angles;

DETAILED DESCRIPTION OF THE PREFERRED EMBODIMENTS

Figure 1:
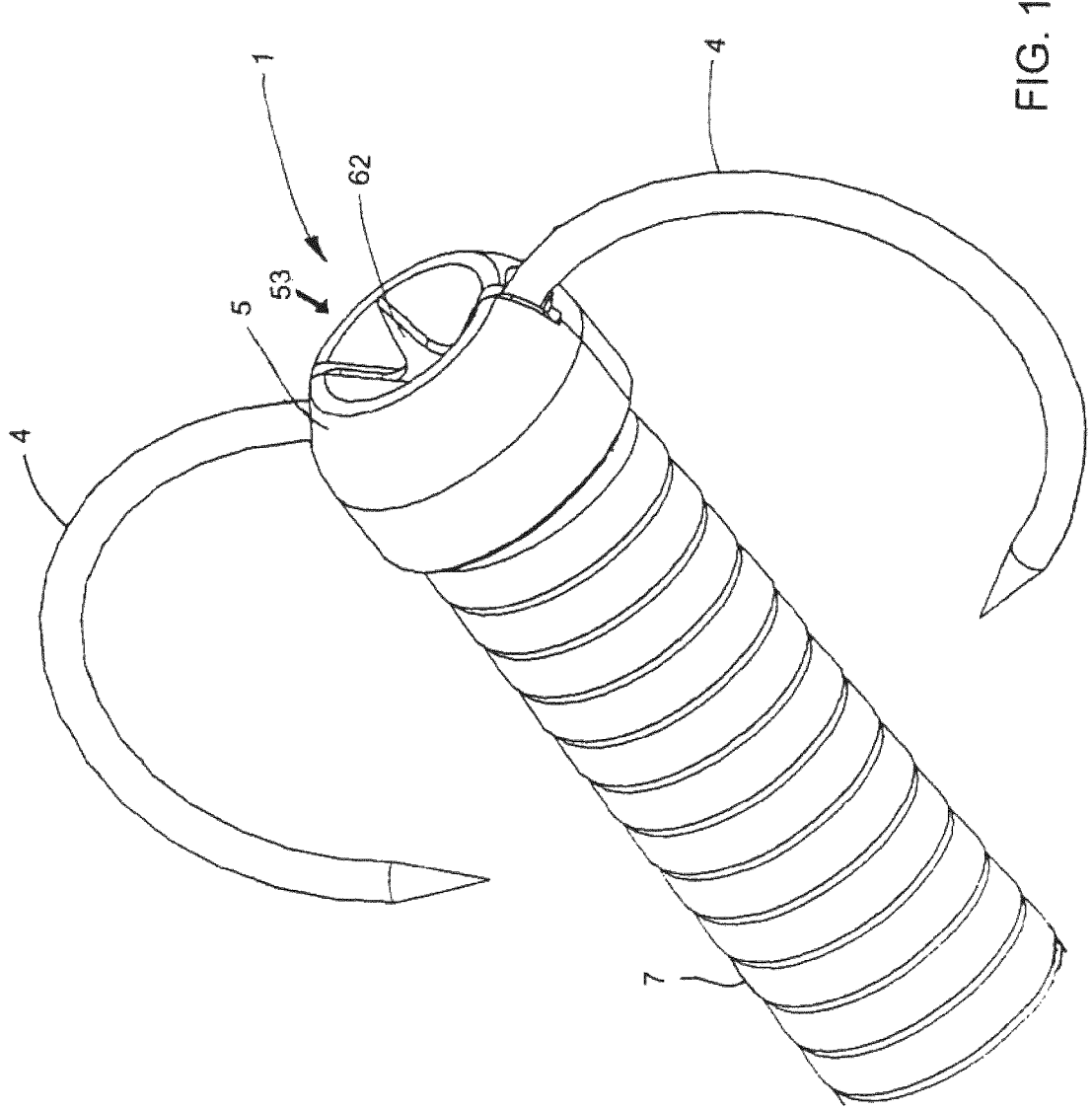
FIG. 1 is a fragmentary, perspective view of a distal end of the flexible tissue retractor according to the invention with needles in a deployed position.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Referring now to the figures of the drawings in detail and first, particularly to FIG. 1 thereof, there is shown a perspective view of a distal portion of a flexible tissue retractor 1 according to the invention with needles 4 in a deployed or extended position. The distal tip 5 of the retractor 1 is hollowed out at its proximal end for reasons that will be explained in further detail below.

Figure 2:
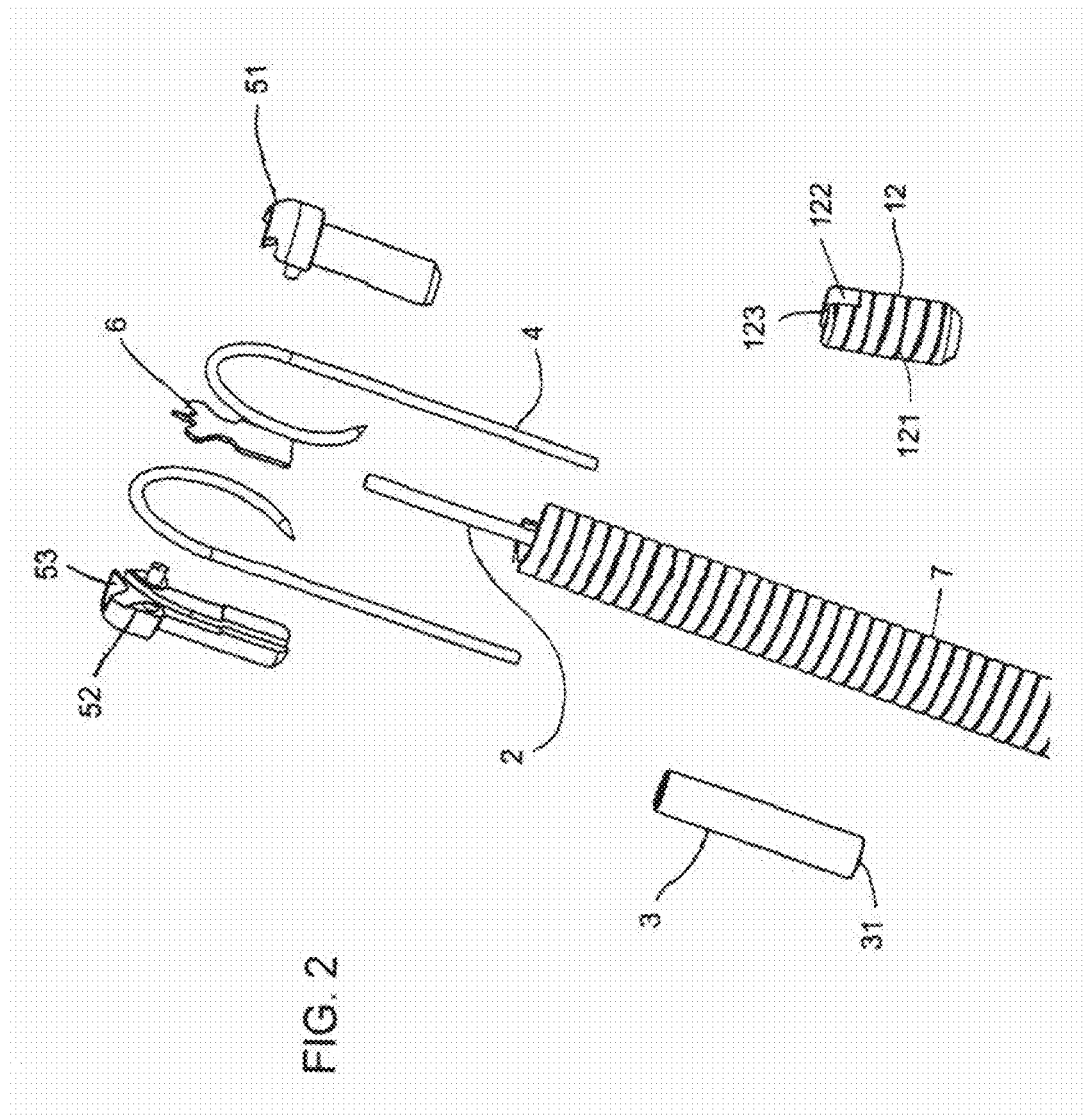
FIG. 2 is a fragmentary, exploded view of components at a distal portion of the retractor of FIG. 1.

FIG. 2 is an exploded view of the distal components of the flexible tissue retractor 1. The distal components include an actuation wire 2, a sleeve 3, two needles 4, two tip halves 51, 52 forming the distal tip 5, a shim 6, a coil winding 7, and a proximal stop 12.

Figure 3:
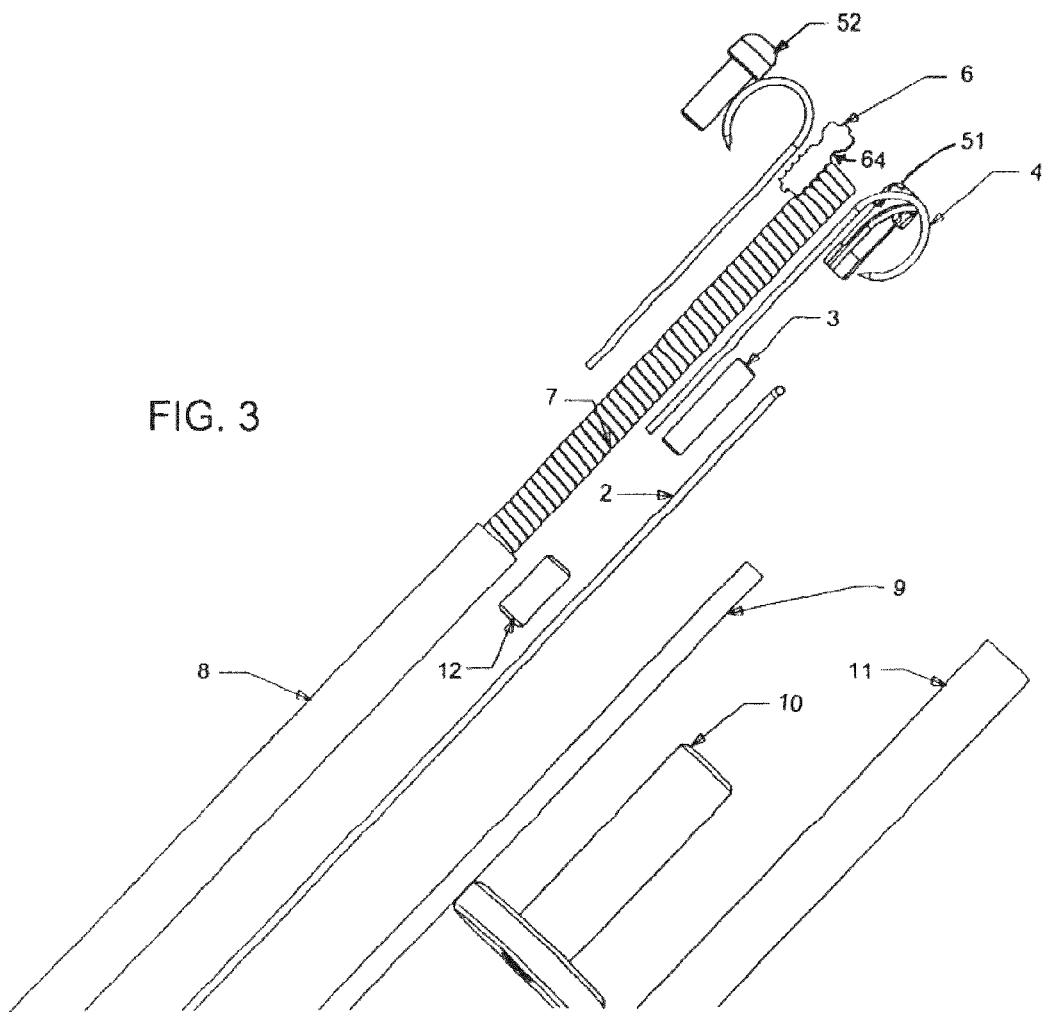
FIG. 3 is a fragmentary, exploded view of the components of a larger portion of the retractor of FIG. 2.

A larger portion of the retractor 1 is shown in the exploded view of FIG. 3, in which an outer jacket 8 surrounds the coil winding 7. Also shown are a sheath 9 (preferably, of polyethylene or TEFLON®), a coil connector 10, and a strain relief 11, each of which will be explained in further detail below.

Figure 4:
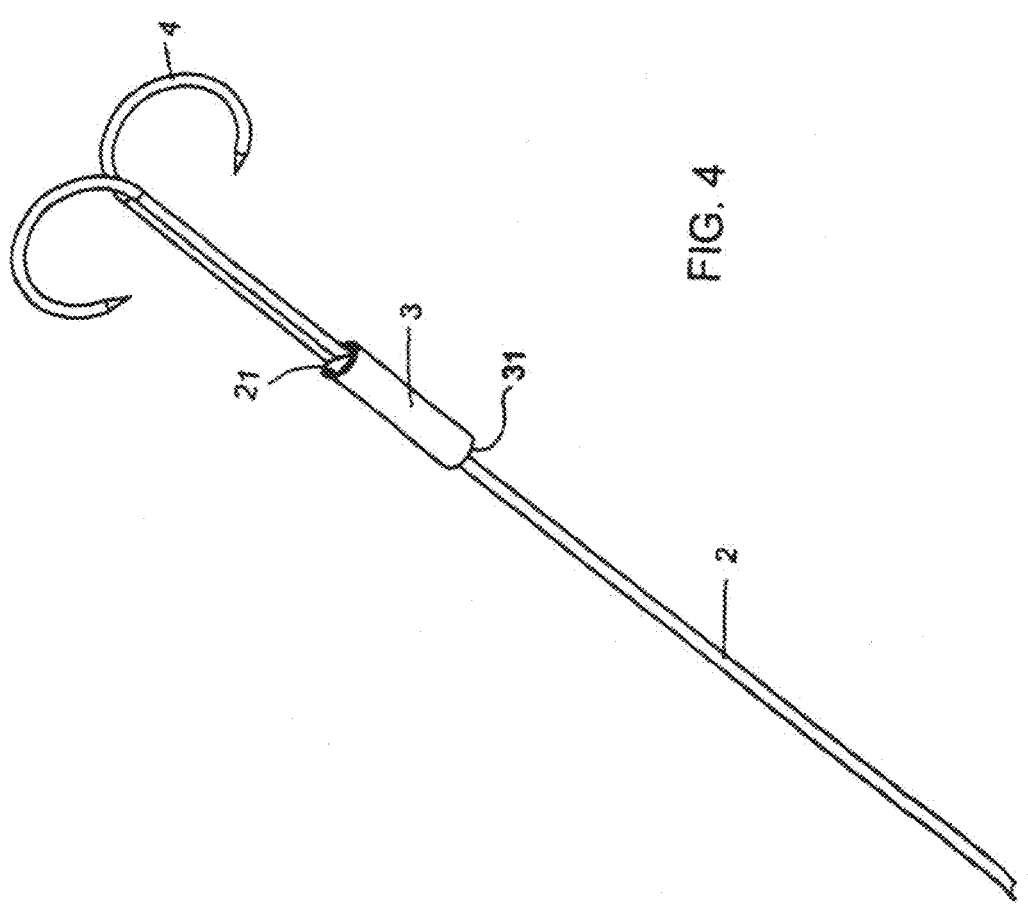
FIG. 4 is a fragmentary, perspective view of a partial assembly of the distal portion components of FIGS. 2 and 3.

FIG. 4 illustrates the connection between the actuation wire 2 and the needles 4. The two needles 4 are inserted in a distal end 31 of the hollow sleeve 3. Also inserted in the distal end 31 is the actuation wire 2. A catch 21, preferably in the form of a bend at the distal-most end of the actuation wire 2, prevents the actuation wire 2 from passing entirely through the sleeve 3. After insertion, the actuation wire 2 and the needles 4 are connected fixedly to the sleeve 3. The preferred embodiment of the retractor 1 has two needles 4. However, the number of needles can be reduced or expanded to suit particular needs.

Preferably, the sleeve 3 is a crimp sleeve that is squeezed by a mechanical stress to fixedly connect the actuation wire 2 to the needles 4. Alternatively, the sleeve 3 can be a heat-contacted sleeve in which heat welds, forms, molds, or otherwise shapes the body of the sleeve 3 to affix the sleeve 3 to both the actuation wire 2 and the needles 4. FIG. 4 also shows the needles 4 in a specifically aligned position with respect to one another that will be discussed in further detail below.

Figure 5:
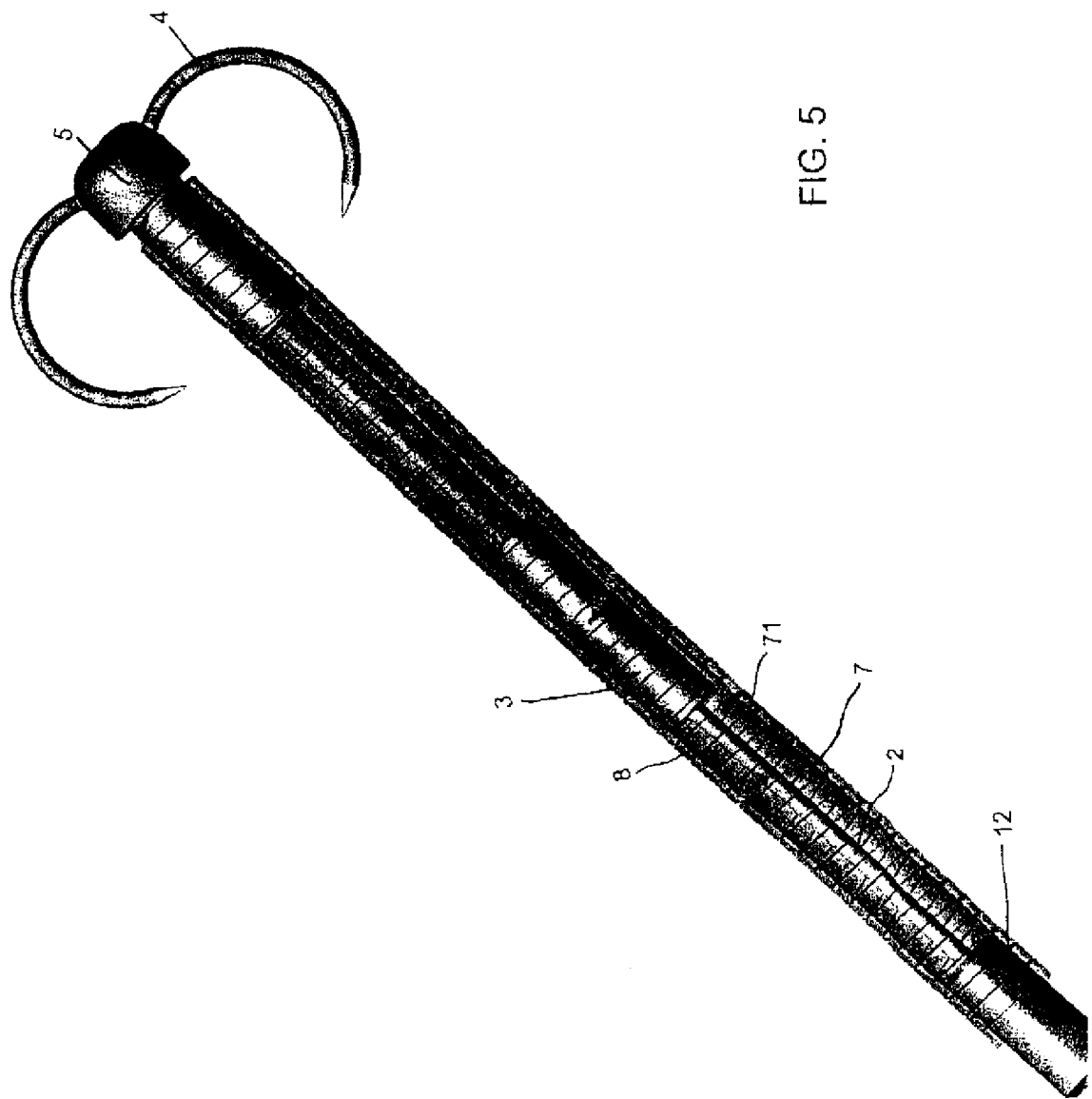
FIG. 5 is a fragmentary, perspective and partially broken away view of the distal portion of the retractor of FIGS. 1 to 3.

The distal portion shown in FIG. 1 is further detailed in the partially broken away view of FIG. 5 to show the interior structure thereof. Therein, the assembly of FIG. 4, including the actuation wire 2, the sleeve 3, and the needles 4, is placed inside the coil winding 7, which is coaxially disposed within the outer jacket 8. The two tip halves 51, 52 clamp the needles 4 therebetween in a clam-like manner, which will be described in further detail below. The proximal stop 12 is located at the proximal end of the distal portion to limit the retraction range of the needles 4.

The coil winding 7 is, preferably, made of an ovular or circular wire that is wound, in the fashion of a tight spring, to provide it with longitudinal strength while having slight longitudinal expandability/give and to provide it simultaneously with radial flexibility or whip. Due to such coiling, the interior of the winding 7 has a natural female thread 71.

The stop 12 is hollow to accommodate the actuation wire 2 slidably therein (in a preferred embodiment, the sheath 9 is not allowed to pass through the stop 12). Thus, the internal diameter of the stop 12 is as least slightly greater than the external diameter of the actuation wire 2. The stop 12 is provided with a male thread 121 on its external surface. A groove 122 is provided at the distal end of the stop 12, the groove 122, preferably, being shaped to accommodate the working end of a flat-head screwdriver.

To load the assembly of FIG. 4 into the distal end of the outer jacket 8 and coil winding 7, the tip halves 51, 52 are clamped upon the needles 4. The stop 12 is inserted into the interior of the coil winding 7 (by threading it therein using rotation of a screwdriver placed in the groove 122) to a given distance. The proximal end of the actuation wire 2 is threaded through the distal end of the coil winding 7 and through the hollow interior of the stop 12. Thus, when the actuation wire 2 is moved proximally, the proximal surface 31 of the sleeve 3 will, ultimately, contact the distal surface 123 of the stop 12 to prevent further proximal movement of the actuation wire 2 and halt retraction of the needles 4.

The tip 5 can be made from a thin walled deep drawn part with a rounded end to maximize the internal diameter of the tip 5, thus allowing for arcuate needles of greater chord height (shorter, smaller radius) to fit within. The exit windows for the needles 4 can be pierced through the wall as part of the deep drawing operation or machined through using various methods including at least one of: wire EDM, laser, conventional milling, etc.

The actuation wire 2 is disposed to deploy and retract the needles 4. As can be seen from FIG. 5, the needles 4 pass through openings on the distal tip 5 to extend out of the distal tip 5. To explain the movement of the needles 4 through the tip 5, FIG. 6 illustrates a preferred configuration of the assembly including the actuation wire 2, sleeve 3, and needles 4 with respect to the tip half 52 and shim 6. FIGS. 1 to 8 show different views of the needles 4, which can move between retracted and extended positions. The entirety of such movement is referred to as selective movement because actuation of the needles is selected by a user anywhere between the fully retracted and fully extended positions.

When the actuation wire 2 is moved proximally in such a configuration, the needles 4 withdraw into the distal tip 5. To explain how the needles 4 move through the distal tip 5, a fragmentary portion of tip half 52 is shown in FIGS. 7 and 8.

FIG. 7 is an enlarged view of a fragmentary distal-most portion of one 52 of the tip halves with a needle 4 accommodated in a track 521. FIG. 8 is similar to FIG. 7 but also shows the relationship of the first needle 4 with respect to the second needle 4' relating to the other tip half 51. As shown in FIG. 7, the track 521 accommodates the needle 4. Thus, when the needles 4 are moved proximally, the needle body 41 is guided through the track 521 and straightened when exiting the track 521 in the proximal direction, indicated by arrow 43. With further proximal movement, the needle tips 42 are, ultimately, fully retracted into the track 521. The stop 12 is positioned to prevent the needle tips 42 from completely exiting the proximal end of the tip 5 and, thereby, rendering the retractor 1 inoperable. The reason why the retractor 1 would be rendered inoperable is because of the unique nature of the needles 4. In the preferred configuration, the needles 4 are made of a flexible shape memory material having a memory shape, in particular, one displaying temperature- and stress-induced martensite. The preferred material is Nitinol, a superelastic Nickel Titanium alloy having the shape memory features as described, for example, in U.S. Pat. Nos. 4,665,906, 5,067, 957, and 5,597,378 to Jervis. The needles 4 are formed to have the memory shape shown in FIGS. 1 to 8 at least at room and body temperature, in particular, above approximately 10° C. Thus, if the needle tips 42 are retracted past the proximal end surface 524 of the tip half 52 (and tip half 51, as well), the needle tips 42 would spring towards their memory shape and completely out of the groove 521 to rest inside the coil winding 7 at the corner defined between the coil winding 7 and the proximal end surface 524 (see, i.e., FIG. 5). In such a position, the bias provided by the shape memory would substantially prevent the retractor 1 from being operated, at least until the retractor was disassembled, fixed, and, thereafter, reassembled.

To allow the tip halves 51, 52 to self-lock around the needles 4, the tip half 52 is formed with two holes 522 and two pins 523. The holes 522 and pins 523 formed in the tip half 52 each respectively fit into corresponding pins and holes formed in the other tip half 51 to fix the two tip halves 51, 52 with one another. In the embodiment shown, the tip halves 51, 52 are not mirror-opposite. Rather, they are identical with respect to the shape of the holes and pins. Of course, any similar fastening device, or combinations thereof, can be used to lock the tip halves 51, 52 to one another, i.e., screws, rivets, catch tabs and slots, and/or catch cylinders and holes.

In an alternative embodiment, it may be desirable to decouple the sleeve 3 from the actuation wire 2 selectively. In such an embodiment, after the distal tip 5 of the retractor 1 is deployed in the tissue, it can be decoupled from the main shaft (including the actuation wire 2, the coil winding 7, the outer jacket 8, and the sheath 9). To accomplish selective decoupling, the distal tip 5 is held loosely in at least one of the coil winding 7 and the outer jacket 8 and the actuation wire is coupled removably to the sleeve 3. For example, the actuation wire 2 can have a male threaded distal end screwed into a female threaded bore in a proximal end of the sleeve 3 and, after deploying the needles 4 in the tissue, the actuation wire 2 is unthreaded, thereby releasing the sleeve 3, with the needles 4 and tip 5, from the retractor 1. Other release devices can be used, such as a crimp of the rod 3 on the actuation wire 3 that is not permanent and can be overcome by a proximally directed force. When the released tip (3, 4, 5) is firmly attached to the tissue it can have application as a marker, suture attachment points for a purse string closure, a tissue apposition suture, and an anchoring point, for example, for various things such as pH probes, miniature capsule cameras, and feeding tubes.

FIG. 6 shows the assembly of the needles 4 with the sleeve 3, the shim 6 and the tip half 5. As set forth above, the shape memory of the needles 4 imparts a force to whatever structure is preventing the needle 4 from being in the defined memory shape. This force also imparts a torque upon a needle 4 when the needle 4 is at least partially deformed by being retracted into the groove 521. The imparted torque, if left unchecked, would move the needle 4 out of the channel 521. Without the shim 6, therefore, the two needles 4 would twist around one another and possibly jump into the other needle's respective groove. To prevent such movement, and to insure that each needle 4 stays within its respective groove 521, the shim 6 is disposed between the two needles 4. In such a position, a flat version of the shim 6 forms an interior first bearing surface 61 for each needle 4 and the groove 521 forms an almost circular exterior second bearing surface for each needle 4. Alternatively, the shim 6 can have a non-illustrated depressed hemispherically cross-sectioned groove corresponding to the groove 521 on each of the tip halves 51, 52. Thus, the groove 521 need not so deeply penetrate the tip halves 51, 52.

The shim 6 has other significant features. First, as shown in FIG. 1, the distal-most end of the shim 6 can have an anchoring spike 62 centered in the hollow 53 of the distal-most end of the tip 5. The function of the anchoring spike 62 is to keep in place and prevent the tip 5 from glancing off a tissue surface (i.e., human tissue, in particular, the wall of the stomach) when the tip 5 of the tissue retractor 1 is pushed initially against the tissue surface. It is noted that the hollow 53 allows the tissue surface to be compressed therein and around the spike 62 to secure the retractor 1 at a grasping location on the surface and prevent radial movement with respect to the spike 62.

In a mechanically efficient manner, the shim 6 can be provided with thread points 63 having a pitch equal to, or slightly different than, a pitch of the interior female thread 71 of the coil winding 7. Accordingly, when the tip 5 is entirely assembled with the shim 6 and needles 4, the thread points 63 can be used as a male thread to secure the tip 5 in the distal end of the coil winding.

The shim 6 also has cutouts 64 to accommodate the shape of the holes 522 and pins 523. These cutouts 64 can be any shape, including, i.e., holes, to accommodate any kind of fastener 522, 523.

The shim 6 may have different profiles and features as shown in FIGS. 9 to 13. FIGS. 10, 12, and 13 show different configurations of the spike 62 and FIG. 11 shows the shim 6 without a spike 62.

In a preferred embodiment, the flexible tissue retractor 1 is an endoscopic device that is passed through the working channel of a flexible endoscope 4000. Use of such an endoscopic retractor 1 is explained in further detail below. In such a procedure, the retractor 1 is used to hold esophageal or any other gastrointestinal tissue 4100, 9100 so that it can be moved or manipulated in some way. As the retractor 1 is passed through one of the working channels 4080 of an endoscope 4000 (see, i.e., FIG. 31), the needles 4 are in a fully retracted position in the tip 5. Once the tip 5 is set into place, it is pushed against the tissue 4100, 9100 (see FIGS. 20 to 27). Preferably, the shim 6 has the anchoring spike 62 (see FIGS. 1, 10, 12, 13, and 31) to help to pinpoint a desired location on the tissue and place the tip 5 at the desired location. Then, the needles 4 are actuated to extend out of the tip 5 and pierce the tissue 4100, 9100. As the needles 4 extend into and curl around the tissue 4100, 9100, it is retained securely (see FIGS. 42 and 43). Now, the tissue 4100, 9100 can be manipulated as required. To release the tissue 4100, 9100, the needles 4 need merely be retracted back into the tip 5. Because the needles 4, made of a shape memory alloy such as nitinol, are pre-formed into the arcuate memory shape, they retain the memory shape through repeated retractions/deployments.

Figure 14:
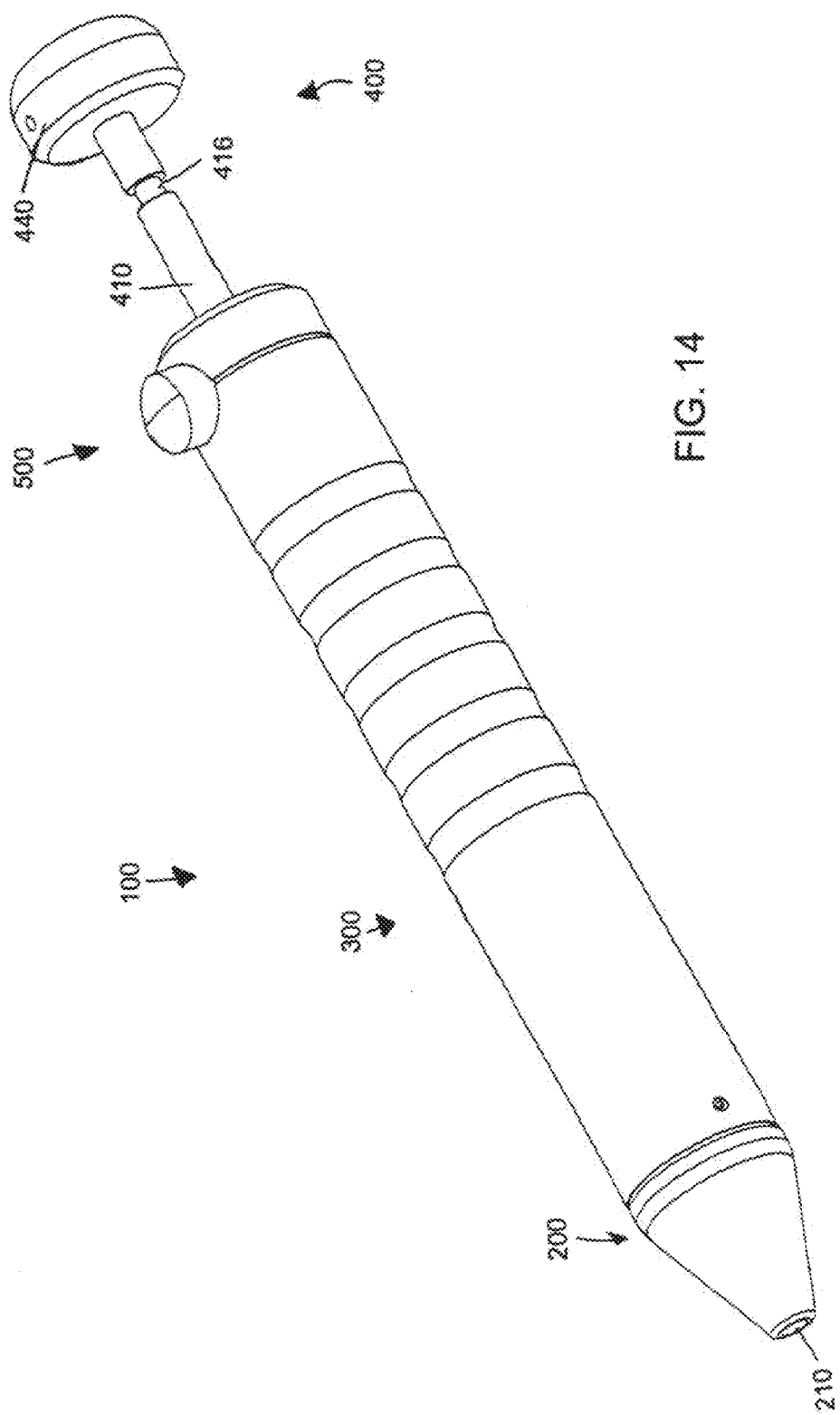
FIG. 14 is a perspective view of a handle at a proximal end of the retractor according to the invention in a retracted position.

FIG. 14 shows a handle 100 of the flexible tissue retractor 1 for controlling the extension and retraction of the needles 4. The handle 100 includes a nose assembly 200, a handle assembly 300, a push-rod assembly 400, and a locking assembly 500.

Figure 15:
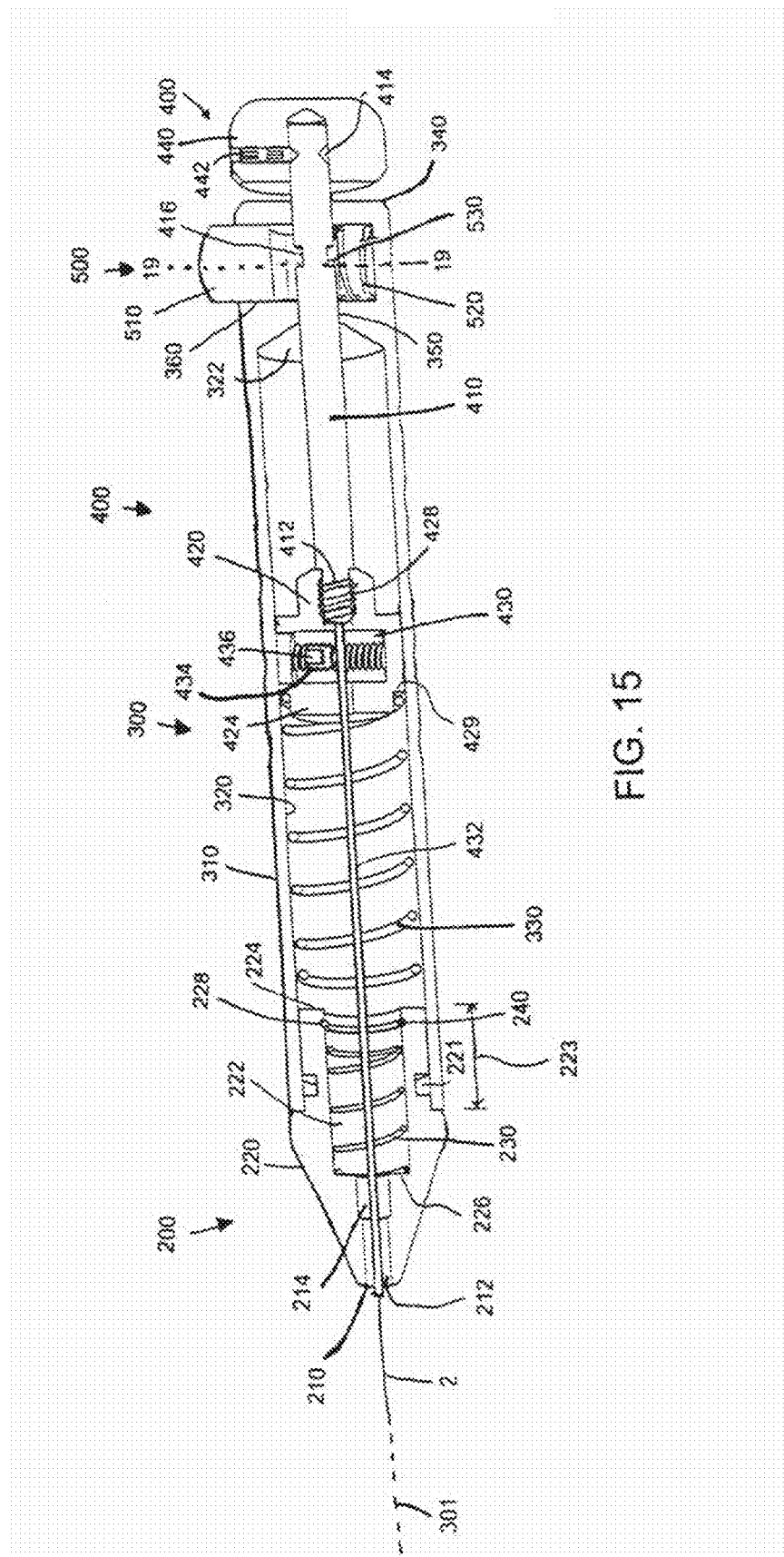
FIG. 15 is a fragmentary, cross-sectional view of some components of the handle of FIG. 14 in a deployed position.

As can be seen from FIG. 15, the nose assembly 200 has a nose 220 defining a distal opening 210 and two coaxial cylindrical hollows communicating with one another including a distal hollow 212 and a proximal hollow 214. The nose 220 has a circumferential exterior setscrew groove 221. The nose 220 also defines a hollow cylindrical interior 222 (communicating with the proximal hollow 214) for receiving therein an over-stroke spring 230 (which has an exterior that is substantially cylindrical-shaped corresponding to the cylindrical shape of the interior 222). The interior 222 has a distal end surface 226 and is defined at the proximal end by a proximal end surface 224 of the nose 220. Adjacent the proximal end surface 224, the interior 222 defines a groove 228, which, preferably, traverses the entire circumference of the interior 222. The groove 228 is used to seat a retaining ring 240 that is used to hold the coil connector 10 within the interior 222 and, thereby, retain the over-stroke spring 230 in place within the interior 222 of the nose 220.

The handle assembly 300 includes a handle body 310 defining a handle body hollow 320 extending along an axis 301 of the handle body 310. A retraction spring 330 is disposed inside the handle body hollow 320. The handle body 310 also defines, near a proximal end 340 thereof, a push-rod hollow 350 and a button hollow 360. The nose 220 is connected removably to the handle body 310 by two setscrews 321 threaded into the handle body 310 and projecting through the handle body hollow 320 and into the setscrew groove 221 (see FIG. 16). The proximal end surface 224 of the nose 220 supports a distal end of the retraction spring 330.

The push-rod assembly 400 is composed of a push-rod 410, a piston 420, a cross-pin 430, a cross-pin tube 432 (also referred to herein as a hypo-tube), and a knob 440. The piston 420 defines a piston hollow 422 (see FIG. 16) preferably having a shape substantially corresponding to the exterior shape of the cross-pin 430. The piston 420 also defines a longitudinal groove or slot 424, extending from the piston hollow 422 to a distal-most end of the piston 420, the slot 424 being shaped to receive the cross-pin tube 432 therein. The cross-pin 430 has an axial bore shaped to receive therein the cross-pin tube 432. The axial bore extends along the axis 301 of the handle body 310. The cross-pin 430 also defines an interior thread 434 extending at least half way through the radial extent thereof (defined by a line orthogonal to the axis 301 when the cross-pin 430 is inserted within the piston hollow 422). Preferably, the thread 432 extends entirely therethrough so that the cross-pin 430 can be inserted into the piston hollow 422 in either orientation. A cross-pin setscrew 436 is threaded within the interior thread 432 and is tightened against the hypo-tube 432 and the actuation wire 2 (when the hypo-tube 432 with the actuation wire 2 therein are threaded into the axial bore of the cross-pin 430) to fixedly retain the two parts to the cross-pin 430.

A button 510 for locking the push rod 410 is installed in the button hollow 360, which is formed near the proximal end of the handle body 310. The button 510 defines a bore 516 having an arch shape shown in FIG. 19. The button 510 is disposed upon a button spring 520, which is also received in the button hollow 360. The button 510 has a transverse bore 512 for receiving a catch pin 530 therein. In an installed position, a contained space 514, defined by the catch pin 530 and the interior surface of the bore 516 in the button 510 enclose the push rod 410 to, thereby, retain the button 510 in the handle body 310.

To assemble the nose assembly 200, the handle assembly 300, the push-rod assembly 400, and the locking assembly 500: the sheath 9 is threaded over the actuation wire 2 and approximately 7 to 10 cm (3 to 4 inches) of actuation wire extends proximally from the sheath 9; the coil winding 7 is threaded over the sheath 9; the outer jacket 8 is threaded over the coil winding 7; and the strain relief 11 is threaded over the outer jacket 8. The nose 220 is threaded over the strain relief 11. The inner diameter of the distal hollow 212 is greater than the outer diameter of the strain relief 11. Therefore, there is play between the nose 220 and the strain relief 11. Now, the over-stroke spring 230 is threaded over the strain relief 11 and is allowed to move freely into the hollow interior 222 of the nose 220. Preferably, the actuation wire 2, the coil winding 7, and the hypo-tube 432 are made of stainless steel. Thus, the sheath is used to prevent the steel actuation wire 2 from rubbing against the steel coil winding 7.

Next, the coil connector 10 is fixedly attached to a sub-assembly including the strain relief 11, the outer jacket 8, the coil winding 7, the sheath 9, and the actuation wire 2. Such attachment occurs, preferably, by crimping 101 the distal end of the coil connector 10. A cross-sectional view of an area surrounding the coil connector 10 is shown in FIG. 18. The crimping does not impart any radial force upon the actuation wire 2. Accordingly, the actuation wire 2 easily slides inside the sheath 9 and with respect to a fixed sub-assembly including the strain relief 11, the outer jacket 8, the coil winding 7, and the sheath 9.

The outer jacket 8 is, preferably, made of heat shrink tubing and is tightly shrunk on to the coil 7. Such a configuration provides a smooth outer surface for the retraction device, and also provides longitudinal stiffness to the shaft. The longitudinal stiffness is important because the needles 4 are deployed by pushing the actuation wire 2 through the shaft of the device, effectively putting the shaft in tension. If the outer jacket 8 was not shrunk tightly to the coil 7, the coil 7 would stretch and the device may not actuate. To that end, it is also important that the coil connector 10 be crimped to the outer jacket 8, over the coil 7, to prevent the coil 7 from stretching during actuation.

Therefore, when fully assembled, the distal hollow 212 and the proximal hollow 214 will receive therein portions of the strain relief 11, the outer jacket 8, the coil winding 7, the sheath 9, and the actuation wire 2. The strain relief 11 is also sized to extend distally out of the opening 210 approximately 10 to 15 cm (4 to 6 inches) to resist impermissible bending of the lumen 7, 8 adjacent the opening 210. In addition, the proximal hollow 214, which is wider in diameter than the distal hollow 212, is formed to receive the distal end of the coil connector 10 when the knob 440 is pressed past a position in the handle body 310 in which the needles 4 are fully extended. Such an extended position is referred to herein as "over-stroke" and will be discussed in further detail below.

To install the coil connector 10 in the nose 220, the proximal surface of the coil connector 10 is pushed to compress the over-stroke spring 230 so that the proximal surface projects into the hollow interior 222 of the nose 220 distally past the groove 228. While holding the coil connector 10 in this position, the retaining ring 240 (which is, preferably, C-shaped with eyelets at each end of the "C" to house, for example, ends of a needle-nose-shaped pliers) is compressed and inserted into the groove 228. Because the retaining ring 240 has a radial expanse sufficient to project inward past the innermost edge of the groove 228, it acts as a proximal stop preventing the coil connector 10 from moving proximally past the retaining ring 240.

In the installed position of the coil connector 10, the actuation wire 2 projects proximally from the proximal end surface 224 of the nose 220. The hypo-tube 432 is threaded over this projecting portion until the two proximal ends thereof are aligned with one another. Then, the aligned ends are threaded into the axial bore of the cross-pin 430 at least up to the interior thread 434 and, preferably, entirely to the opposite side of the interior thread and through the other side of the axial bore. The aligned ends can project slightly out the proximal side of the axial bore because there is a distance between the proximal side of the cross-pin 430 and the distal end of the installed push-rod 410. To connect the actuation wire 2 and the hypo-tube 432 fixedly to the cross-pin 430, the cross-pin setscrew 436 is rotated inward until a sufficient force is exerted upon the hypo-tube 432 to prevent the hypo-tube 432 and the actuation wire 2 from being removed from the crosspiece 430.

The retraction spring 330 can be threaded over the actuation wire 2 before the cross-pin 430 is fastened to the hypotube 432 or thereafter because the internal diameter of the retraction spring 330 is similar to or greater than the diametric length of the cross-pin 430 (length of cross-pin 430 along a diameter orthogonal to the actuation wire 2 and the axis 301). The retraction spring 330 is, then, compressed sufficiently far to allow the cross-pin 430 to be inserted into the piston hollow 422, thereby, sliding the hypo-tube 432 into the longitudinal slot 424 of the piston 420. In such a position, both the overstroke spring 230 and the retraction spring 330 are preloaded. The pre-compression of the retraction spring is set such that the pre-compression force is great enough to always retract the needles during use of the retractor device. The over-stroke spring 230 pre-compression is set such that the force required to advance the needles 4 does not exceed the pre-compression force. That way, the needles 4 will advance positively and fully before the over-stroke spring 230 begins to compress due to over stroking In such a configuration, the retraction spring 330 is disposed between the proximal end surface 224 of the nose 220 and the distal end surface 429 of the piston 420 to bias the piston 420 towards the knob 440.

The distal male threaded end 412 of the push rod 410 is screwed into female threads 428 of the proximal end of the piston 420. As such, the piston 420 form-lockingly engages the push-rod 410. A form-locking connection is one that connects two elements together due to the shape of the elements themselves, as opposed to a force-locking connection, which locks the elements together by force external to the elements. Thus, axial movement of the actuation wire 2 linearly follows axial movement of the piston 420.

Figure 16:
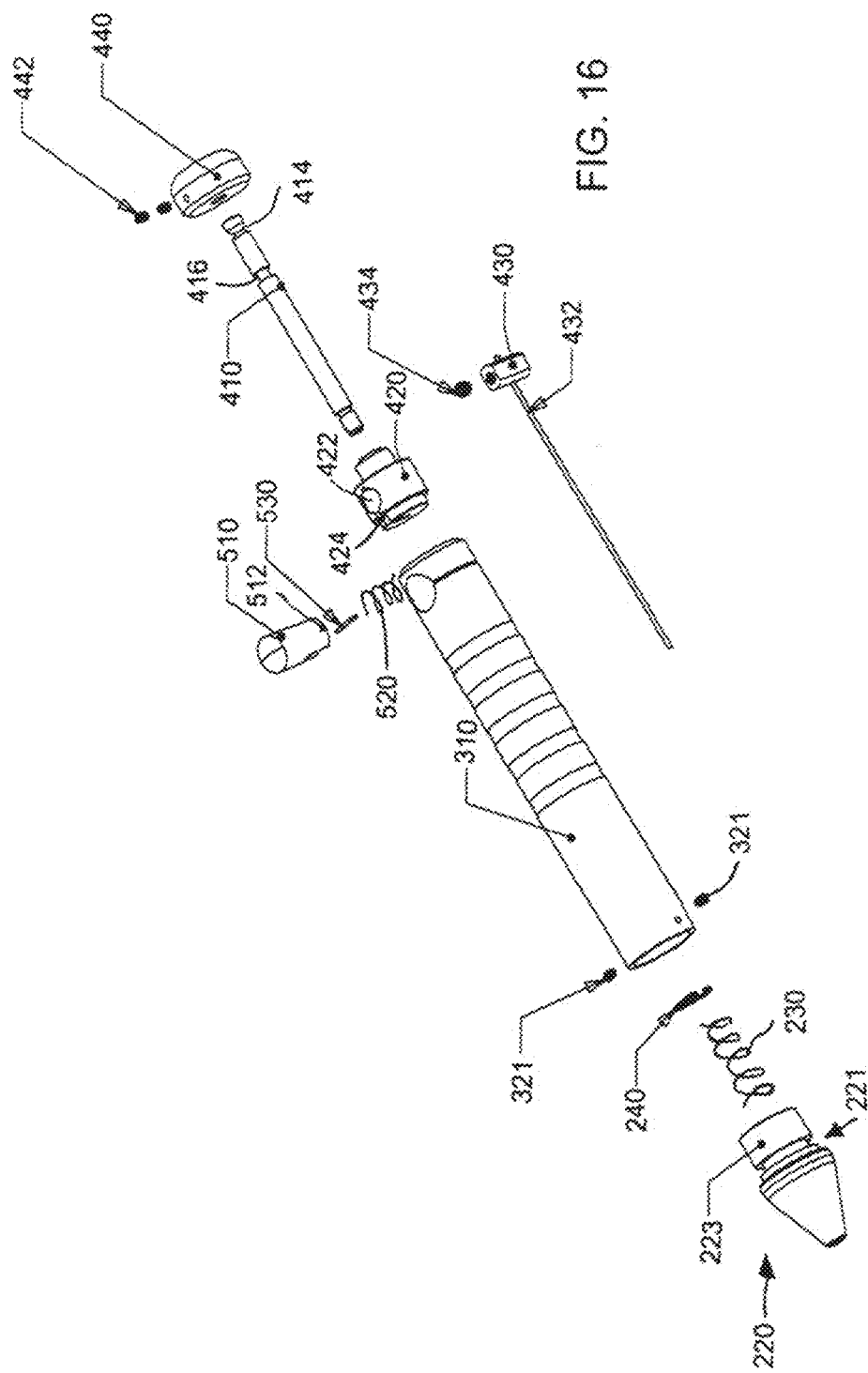
FIG. 16 is an exploded view of some of the components of the handle of FIG. 14.

Now, the handle body 310 is distally threaded over the proximal end of the push-rod 410, over the piston 420, over the retention spring 330, and, finally, snugly over the proximal stub 223 of the nose 220 and secured thereon by at least one setscrew 321 (see FIG. 16). Before the proximal end of the push-rod 410 enters the button hollow 360, however, the button spring 520 is inserted in the button hollow 360 and the pre-assembled the button 510 (catch pin 530 inserted into the transverse bore 512 as shown in FIG. 19) is pressed against the button spring 520 to compress the spring to such an extent that the contained space 514 (between the catch pin 530 and the interior surface 516 in the button 510) is aligned approximately with the axis 301 and, therefore, with the axis of the push-rod 410. In such a position, the proximal end of the push-rod 410 will pass through the contained space 514 without substantial friction and project out of the proximal end of the handle body 310. It is noted that, to assist threading of the proximal end of the push-rod 410 into the proximal end of the handle body 310, the proximal surface 322 of the handle body hollow 320 is tapered towards the push-rod hollow 350.

Figure 17:
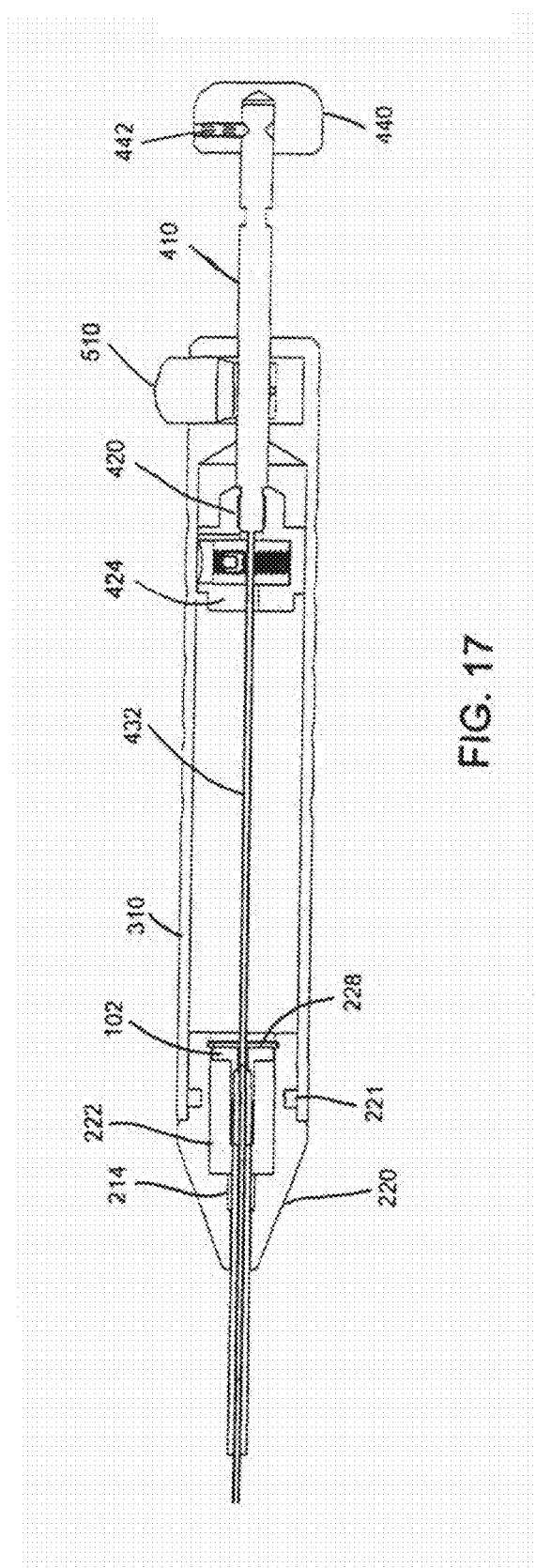
FIG. 17 is a fragmentary, cross-sectional view of some components of the handle of FIG. 14 in the retracted position.

The proximal end of the push-rod 410 is formed with a circumferential set-pin groove 414 to accommodate a knob set pin 442 that fixedly connects the knob 440 to the push-rod 410. In an alternative non-illustrated embodiment, the proximal end of the push-rod 410 can be formed with a male thread that corresponds to a female thread in the knob 440 such that the knob 440 is screwed onto the push-rod 410. The push-rod 410 is also formed with a circumferential catch pin groove 416 used to capture the catch pin 530 when the push-rod 410 is pressed from a proximal position shown in FIGS. 14 and 17 to a distal position shown in FIGS. 1, 5, and 15. In the proximal position, the needles 4 are retracted within the tip 5 and, in the distal position, the needles 4 are extended out of the tip 5. When the catch pin 530 is within the groove 416, the needles 4 are in the distal position and the knob 440 can only be moved slightly; such movement is permitted by the play created by the length of the groove 416 along the longitudinal extent of the push-rod 410. A user can selectively engage the button 510 to capture the push-rod 410 with the catch pin 530 or allow the push-rod 410 to move freely in the longitudinal direction by pressing the button 510 to move the catch pin 530 out of the way so that the groove 416 does not engage the catch pin 530. Accordingly, the locking function of the button 510 can be said to selectively retain the needles 4 in a given position. Of course, there can be a plurality of spaced apart grooves 416 to provide different retention positions from that illustrated, for example, in FIG. 11.

It is noted that the distal end of the hypo-tube 432 rests proximal of the distal end of the coil connector 10 when the piston 420 is in a proximal-most position and rests distal to the distal opening 210 of the nose 220 when (as shown in FIG.

15) the knob 440 is pressed to a distal position such that the catch pin 530 engages the catch pin groove 416, this distal position corresponding to a position in which the needles 4 are completely extended out from the tip 5 as shown in FIG. 1. The distal position shown in FIG. 15, however, is not the distal-most position of the knob 440. Such a feature is intentional because of the nature of the retractor 1 being an assembly that is intended to be inserted into a patient (in particular, through an endoscope) and, therefore, is curved because of the natures of the patient and the endoscope.

Geometry of the co-axially placed actuation wire 2, sheath 9, coil winding 7, and outer jacket 8 dictates that when the outer jacket 8 and/or the coil winding 7 is bent (as it traverses through an endoscope, for example) the length of the actuation wire 2 needed to traverse the curved lumen 7, 8 increases. The actuation wire 2 is configured, therefore, to be sufficiently long such that over-stroke does not occur when the lumen 7, 8 are curved in use. However, when the coil winding 7 and the outer jacket 8 are straight, the operation of the push-rod 410 may cause over-stroke because the actuation wire 2 is longer than the lumen 7, 8 surrounding the actuation wire 2. In such a case, there arises the above-mentioned danger of needle over-extension, which could cause damage to the tissue to be retracted or to the needles 4 themselves. To compensate for the over-stroke, the nose assembly 200 is provided with the over-stroke spring 230, which is disposed in the hollow interior 222 of the nose 220. The over-stroke spring 230 is supported at its distal end by the distal end surface 226 of the hollow interior 222 and at its proximal end by the distal surface 104 of a head 102 of the coil connector 10 (see FIG. 18). Such a configuration, effectively, decouples the lumen 7, 8, 9 (and 11) from the actuation wire 2. To fully deploy the needles 4 in an over-stroke situation, the knob 440 must be pressed in more than if the lumen 7, 8 were curved. Accordingly, the over-stroke spring 230 has a k-factor tuned to allow full deployment of the needles 4 and, thereafter, to compress for further distal movement and compensate for the over-stroke. Due to this tuning of the over-stroke spring 230, the coil winding 7, through the coil connector 10, will compress against the over-stroke spring 230 and move the entire sub-assembly of the lumen 7, 8, and 9 distally and, thereby, absorb the over-stroke of the push-rod 410. Thus, the over-stroke spring 230 functions as a buffer to absorb any over-stroke of the push-rod 410 and substantially prevents any disadvantageous affects when in use. Specifically, the over-stroke spring 230 protects the needles 4 from over-extending and protects the coil winding 7 from being over extended. Most of the time, the coil winding 7 and the outer jacket 8 will be curved during operation. The coil winding 7 and the retraction spring 330 are constructed to provide proper extension for the needles 4 in such a situation.

When pushing the knob 440, the retraction spring 330 will be compressed and the needles 4 will be extended out of the tip 5 by the actuation wire 2. After the needles 4 are extended to a certain distance, the catch-pin 530 will fall into the catch-pin groove 416 formed on the push-rod 410, thus preventing the push-rod 410 from further movement and locking the needles 4 in the deployed position (assuming that the button 510 is not being depressed). Because the needles 4 are held in the deployed position, the user is, then, free to let go of the handle without the fear of needle 4 retraction, and to use their hands for other surgical procedures until retraction of the needles 4 is desired. By pressing the button 510 down, the catch-pin 530 is forced out of the catch-pin groove 416, thereby unlocking the push-rod 410 and automatically retracting the needles 4 because the retraction spring 330 imparts a proximally directed bias to the piston 420.

By way of example only, preferred dimensions for one exemplary handle 100 are set forth in the following text. An overall longitudinal length of the handle 100 is, preferably, approximately 17 cm (6.74 inches). A preferred longitudinal length of the handle body 310 is between approximately 13 and 14 cm (5.29 inches). A preferred distance between the distal surface of the knob 440 and the proximal end surface of the handle body 310 is between approximately 2.5 and 3 cm (1.05 inches).

The operation of the flexible tissue retractor 1 of the invention will be described in the following text with respect to FIGS. 20 through 27.

The needles 4 are fully retracted into the tip 5 of the retractor 1 as the retractor 1 passes through the endoscope. Using the camera of the endoscope, the tip 5 is positioned at the desired location, in particular, in a selected location of the wall of the stomach. The spike 62 is used to keep the tip 5 in position once the tip 5 is advanced to contact the mucosa 202, the innermost layer of the stomach.

It is most desirable, in the treatment of Gastroesophageal Reflux Disease, to grasp the muscularis 204 of the stomach, which is the middle layer next to the mucosa 202. It is not desirable, for the reasons stated above, to grasp the serosa 206 of the stomach (the outermost layer). Therefore, the memory shaped curvature of the needles 4 is configured so that penetration will occur to a depth no greater than the muscularis 204. Such assurance is illustrated with regard to FIGS. 20 to 27.

Once in place in the stomach, the tip 5 is pushed against the mucosa 202 and the needles 4 are extended out of the tip 5 to pierce the stomach tissue with the goal of reaching the muscularis 204. The piercing depth of the needles 4 is dependent upon the degree in which the tip 5 is pressed against the mucosa.

If the tip 5 is pressed against the mucosa 202 such that the mucosa 202 presents a 160° angle to the distal face of the tip 5, as shown in FIG. 20, the needles 4 will barely penetrate the mucosa 202 or will not penetrate the mucosa 202 at all.

If the tip 5 is pressed against the mucosa 202 such that the mucosa 202 presents a 120° angle to the distal face of the tip 5, as shown in FIG. 21, the needles 4 will penetrate the mucosa 202 but will barely penetrate the muscularis 204 or will not penetrate the muscularis 204 at all.

If the tip 5 is pressed against the mucosa 202 such that the mucosa 202 presents a 90° angle to the distal face of the tip 5, as shown in FIG. 22, the needles 4 will penetrate the muscularis 204 sufficiently far for a proper retraction.

If the tip 5 is pressed against the mucosa 202 such that the mucosa 202 presents a 75° angle to the distal face of the tip 5, as shown in FIG. 23, the needles 4 will penetrate the muscularis 204 sufficiently far for a proper retraction.

If the tip 5 is pressed against the mucosa 202 such that the mucosa 202 presents a 60° angle to the distal face of the tip 5, as shown in FIG. 24, the needles 4 will penetrate muscularis 204 sufficiently far for a proper retraction.

If the tip 5 is pressed against the mucosa 202 such that the mucosa 202 presents a 45° angle to the distal face of the tip 5, as shown in FIG. 25, the needles 4 will penetrate more than a majority of the muscularis 204 for a proper retraction but still far short of the serosa 206.

If the tip 5 is pressed against the mucosa 202 such that the mucosa 202 presents a 30° angle to the distal face of the tip 5, as shown in FIG. 26, the needles 4 will penetrate more than a majority of the muscularis 204 for a proper retraction but still not as far as the serosa 206.

If the tip 5 is pressed against the mucosa 202 such that the mucosa 202 presents a 5° angle to the distal face of the tip 5, as shown in FIG. 27, the needles 4 will penetrate more than a majority of the muscularis 204 for a proper retraction but still just before the serosa 206.

Of course, the actual degree of penetration will be dependent on the thickness of the mucosa 202 at the given retraction site and upon the respective thicknesses of the patient's stomach layers 202, 204, 206. Nonetheless, the sizing of the needles' curvature should behave as stated above for non-abnormal patients.

The retractor 1 can be configured to selectively grasp a desired number of layers (202, 204, 206) depending upon the curve of the needles 4 and the size and/or orientation of the track 521 exit. Particularly with regard to stomach tissue, the retractor 1 can be used to selectively grasp the mucosa 202 (see FIGS. 20 to 27) and lift it from the muscularis 204, thus enabling and simplifying mucosal resection. In the case of forming a full thickness plication in the stomach, the stronger muscular layer of the gastric wall must be grasped to ensure that the full thickness of the wall will be retracted when forming the plication (see FIGS. 32, 33, and 43 to 45). By tailoring the needles 4 and the way in which they exit from the tip 5 of the retractor 1, the retractor 1 can be made to selectively grasp the different layers in the gastric wall. Being able to grasp a specific layer of the gastrointestinal wall is advantageous depending on the requirements of the specific procedure being performed.

When retracted properly, the tissue can be manipulated or moved as required. Release of the tissue, by retracting the needles 4 back into the tip 5, occurs simply by a press of the button 510.

The needles 4 are dimensioned and shaped such that they will most likely not enter the serosa 206. As shown in FIGS. 20 to 27, no matter how hard the tip 5 is pushed against the stomach tissue, the needles 4 will stay safely within the serosa 206 and only pierce the mucosa 202 and muscularis 204, thereby insuring that insertion of a GERD fastening clip will be implanted in the most optimal position within the patient.

Figure 28:
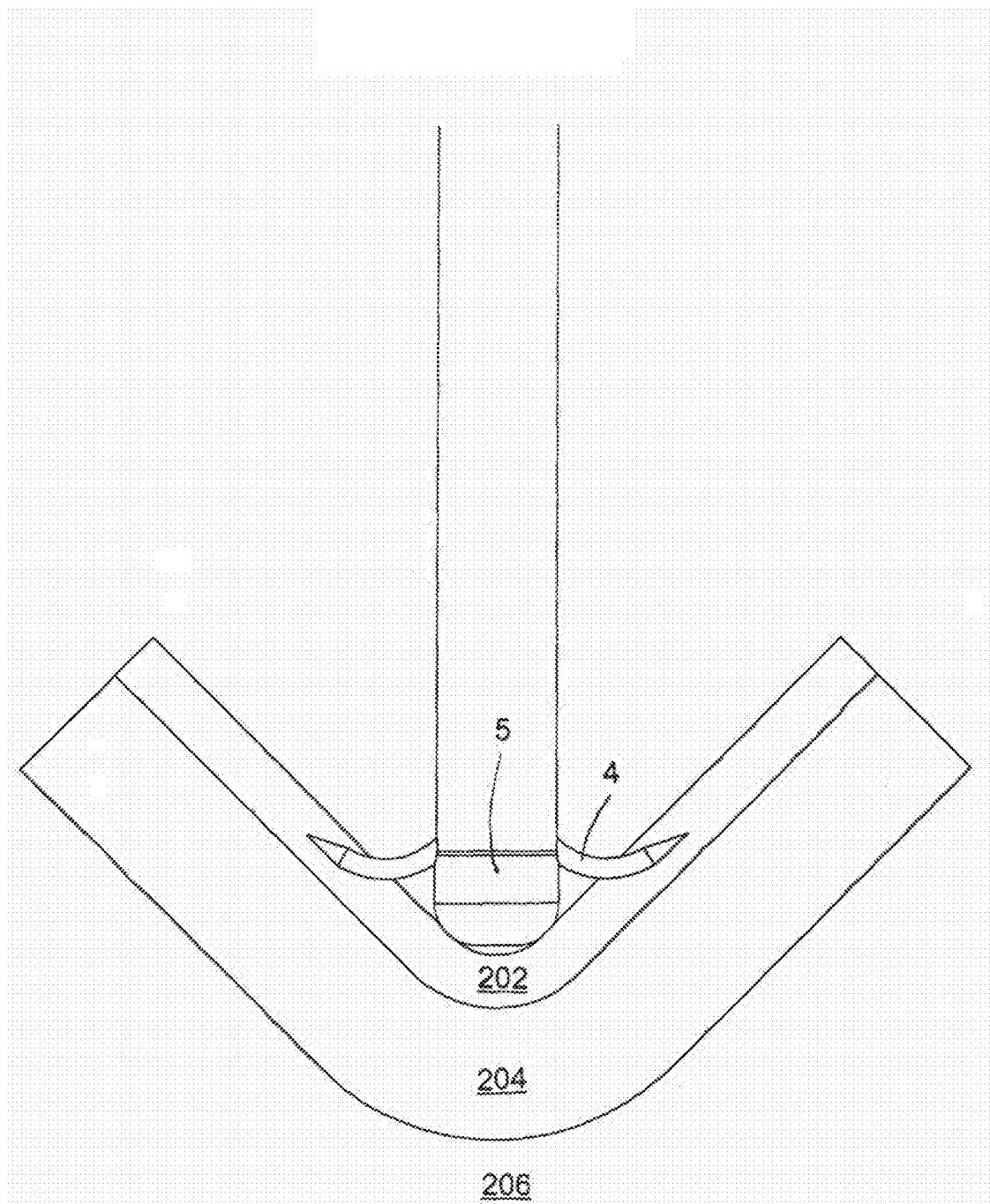
FIG. 28 is a fragmentary, partially cross-sectional and partially plan view of the method of using the retractor according to the invention with needle exit windows more proximal to the tip than in FIGS. 20 to 27.

By varying the position of the needle exit locations and/or the angle of exit at the tip of the retractor 1, the needles 4 can be made to extend proximal to a plane at the tip of the retractor 1 and orthogonal to the longitudinal axis of the tip 5 or distal to the plane. Further, by varying the length and/or the radius of curvature of the needles 4, the depth of penetration in the tissue can be limited or enhanced. If the needles 4 exit proximal to the tip plane, their depth of penetration will be limited. Such an example is shown in FIG. 28. Conversely, if the needles 4 extend beyond the plane, their depth of penetration will be enhanced. If the needles 4 are longer and with a greater radius of curvature, the penetration will be enhanced, while conversely, if they are short and the radius of curvature is decreased, the penetration will be limited. By varying the combinations and dimensions of these parameters, the retractor 1 can be tailored to penetrate the tissue in different ways, allowing the grasping of specific layers of the tissue to suit the procedural requirements.

In the case of the endoscopic treatment of GERD, experience has shown that a user can tell whether or not the retraction of the stomach wall is proper, in other words, both the mucosa 202 and muscularis 204 are retracted. The retracted stomach tissue exhibits a significantly different shape when both the mucosa 202 and muscularis 204 are retracted as compared to when only the mucosa 202 is retracted. The mucosa 202 is analogous to a bag within a bag in that the mucosa 202 is not truly attached to the muscularis 204 and, therefore, when only the mucosa 202 is retracted a clearly visible and sharply slanted peak is formed by the retracted mucosa 202. In contrast, when both the mucosa 202 and muscularis 204 are retracted, a clearly visible and smoothly sloped hill is formed. The visual confirmation assures that at least the muscularis 204 was grabbed and the size and shape of the needles 4 ensures a reduction of the possibility of perforating the serosa 206. The serosa 206, unlike the mucosa 202, is truly attached to the muscularis 204. It is a very thin layer and, thus, moves with the muscular layer.

Figure 29:
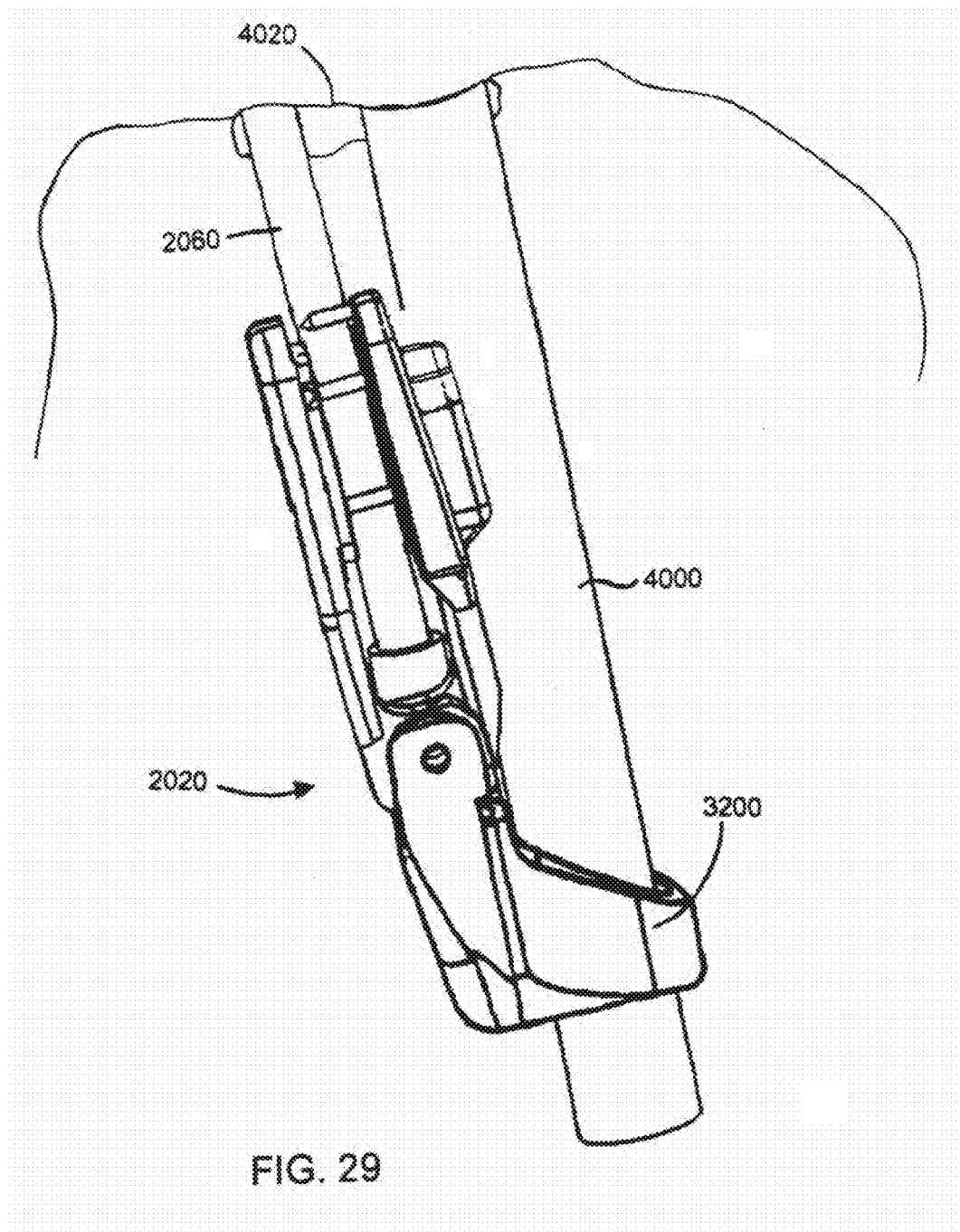
FIG. 29 is a fragmentary, side view of a plication device coupled to an endoscope during insertion of the two into the stomach.

According to a method of the present invention, the retractor 1 may be operated as follows with respect to the treatment of GERD. Turning to FIG. 29, a sleeve 3200 of a distal end effector 2020 is slidably coupled over the distal end of an endoscope 4000 and the end effector 2020 is slid proximally over the endoscope 4000. The distal end of the endoscope 4000 is, then, inserted into the tracheopharangeal passage and moved through the esophagus 4140 and into the stomach 4160, with the end effector 2020 of the plication instrument mounted, preferably, approximately 20 cm back from the distal end of the endoscope 4000. The actuating handle and/or control shaft 2060 are, then, manipulated in gross to slide the distal end effector 2020 over the distal end of the inserted endoscope 4000 and into the stomach 4160, with the endoscope 4000 functioning as a guidewire for the sleeve 3200. Optionally, the endoscope 4000 may be retroflexed to look back toward to the LES 4020 of the esophagus 4140 and visualize the advancement of the end effector 2020.

Figure 30:
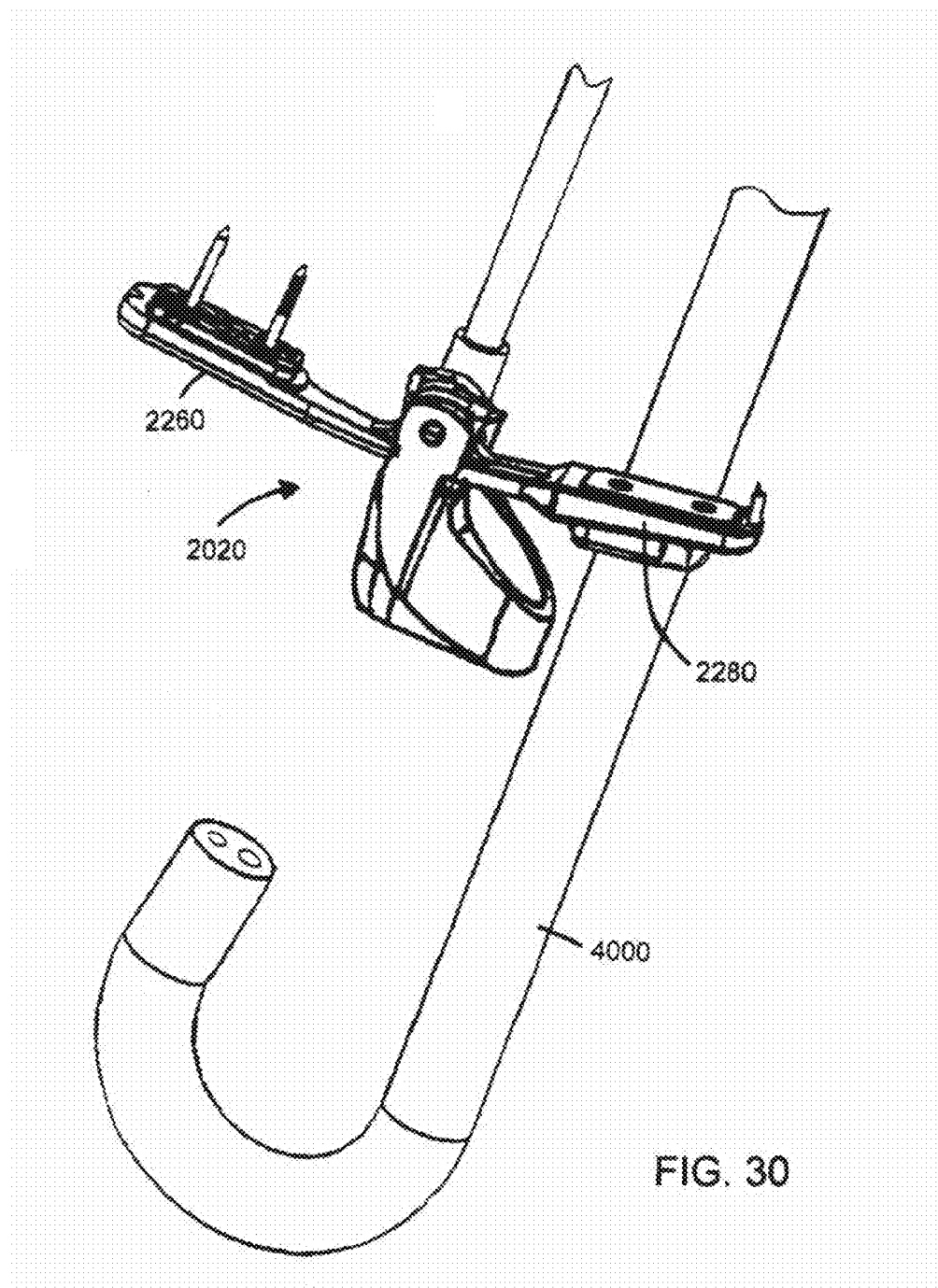
FIG. 30 is a fragmentary, perspective side view of the plication device separated from the endoscope and shown with the jaws in an open position.

If the endoscope is retroflexed during insertion of the distal end effector 2020, the passage of the distal end effector 2020 into the stomach 4160 is performed under view of the endoscope 4000. Once the distal end effector 2020 is located in the stomach 4160, the endoscope 4000 is, preferably, straightened if it was retroflexed, and the end effector 2020 is moved distally off the endoscope 4000 such that the endoscope 4000 and clip implantation instrument are completely separated. Referring to FIG. 30, the endoscope 4000 is then, again, retroflexed and the actuating handle is operated to open the jaws 2260, 2280 of the end effector 2020.

Figure 31:
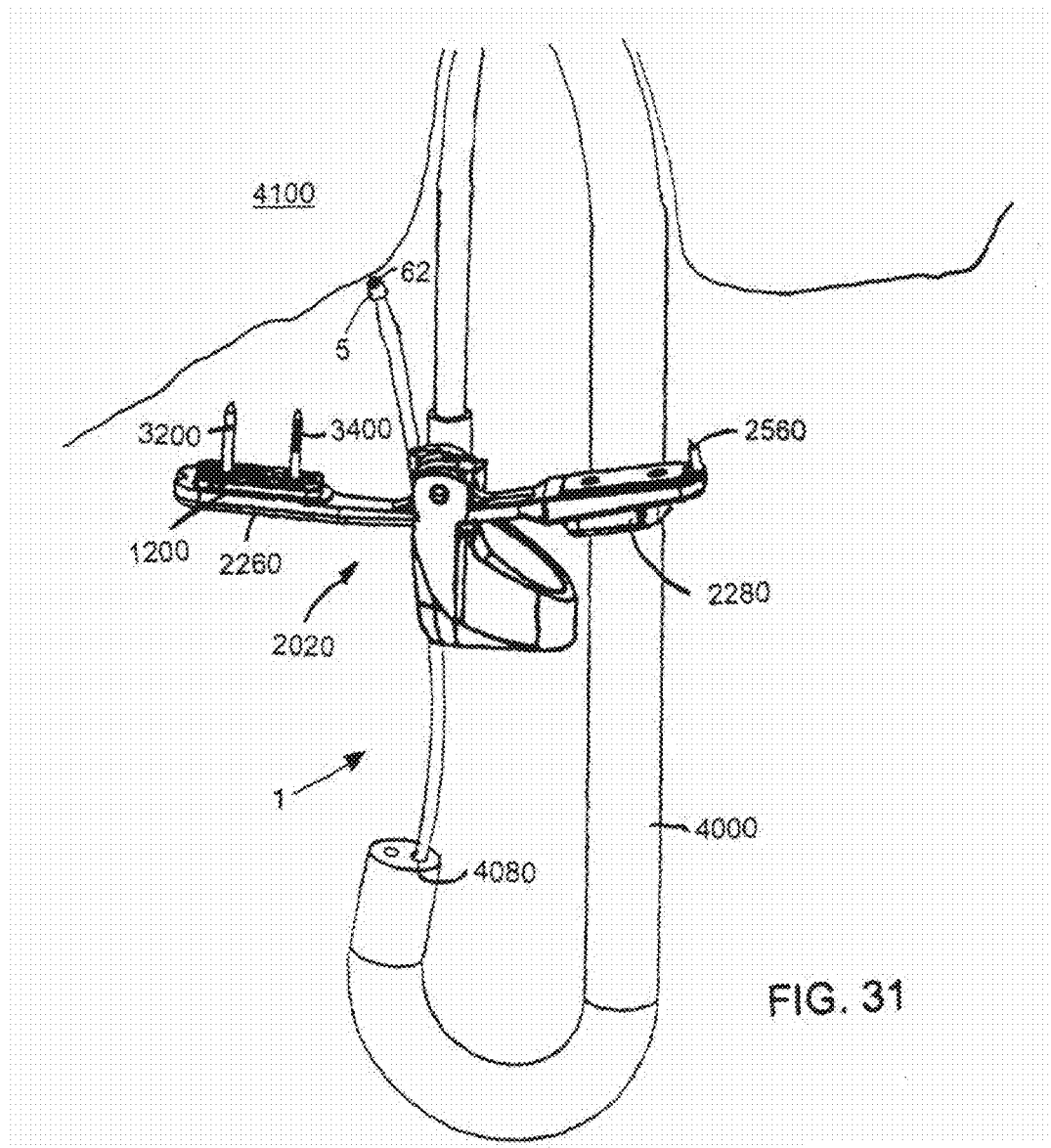
FIG. 31 is a fragmentary, perspective side view similar to FIG. 30, and additionally shows the retractor according to the invention advanced through the endoscope and engaging the target tissue at which a plication is desired to be made.

Referring to FIG. 31, a retractor 1 according to the present invention is, preferably, then inserted through a working channel 4080 of the endoscope 4000 and directed at target tissue 4100 one to three centimeters into the stomach 4160 adjacent the LES 4020 where the center of a plication is to be located. The retractor 1 engages the tissue 4100 and pulls the tissue 4100 back between the jaws 2260, 2280 of the end effector 2020 of the clip implantation instrument. The retractor 1 engages the deep muscle of the stomach wall, thus retracting a full thickness plication of the stomach wall between the jaws. In addition, the actuating handle and/or control shaft 2060 of the clip implantation instrument are pulled back in gross (i.e., in the direction of withdrawing the instrument) such that the jaws 2260, 2280 approach the tissue 4100 in a direction substantially parallel to the esophagus 4140. This is a highly desirable angle of approach that has been previously unattainable with endoscopic GERD treatment instruments. That is, any device that retroflexes must extend through an arc of a minimum radius. This radius is such that when retroflexed therethrough, the distal end of the device will be displaced thereby, and, thus, the end effectors will be further away from the GEJ than from a device that does not require retroflexion. It is not possible, therefore, for a retroflexed device to be both parallel to an entry path and also not displaced at least a couple of centimeters away from the entry path.

Figure 32:
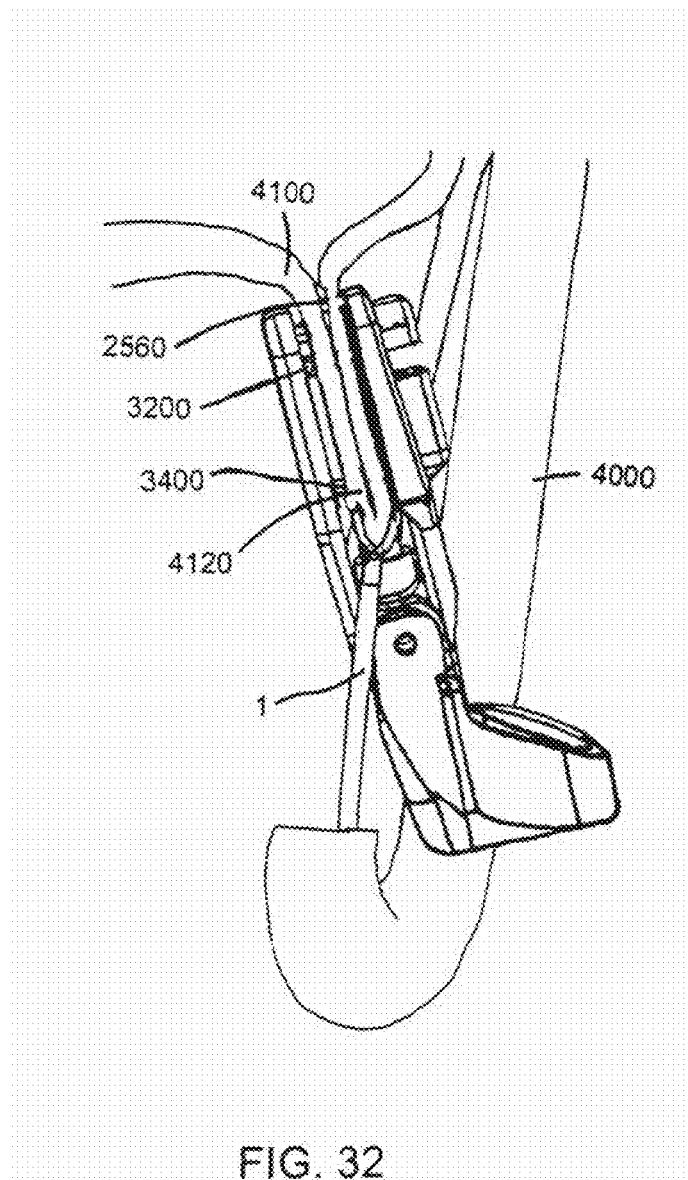
FIG. 32 is a fragmentary, perspective side view shown with the jaws of the plication device plicating the target tissue and a plication fastener in a locked configuration.

A proximal actuation handle is, then, operated to cause the jaws 2260, 2280 to close, as shown in FIG. 32. As a central point of the tissue 4100 is held in a fixed location between the jaws 2260, 2280 by the retractor 1 during movement of the jaws 2260, 2280, a tissue plication 4120 is formed by the jaws

2260, 2280 as the male and female parts 1200, 1400 of the fastener 1000 are brought together with the plication 4120 clamped therebetween. When the jaws 2260, 2280 are closed about the tissue plication 4120, the posts 3200, 3400 of the male part 1200 of the fastener 100, preferably, pierce the tissue 4100 through the serosal layers of the plication forming a serosa-to-serosa contact on the inside surfaces of the plication. The piercing post 2560 of the female jaw 2280, preferably, pierces through the deep muscle of the tissue 4100 sufficiently to hold the tissue 4100 in place while the jaws are closed. Experimental procedures have shown that such contact results in tissue adhesion after healing such that the tissue 4100 is permanently reconfigured, i.e., even if the fastener 1000 is removed later. In this manner, a zone of reduced compliance is created about the LES 4020.

The location and size of the plication 4120 as well as the relative positions of the fastener parts 1200, 1400 are observed through the endoscope 4000. Moreover, more or less clamping pressure can be applied to the plicated tissue by control of a proximal actuation handle until full penetration by the male posts has been achieved.

Figure 33:
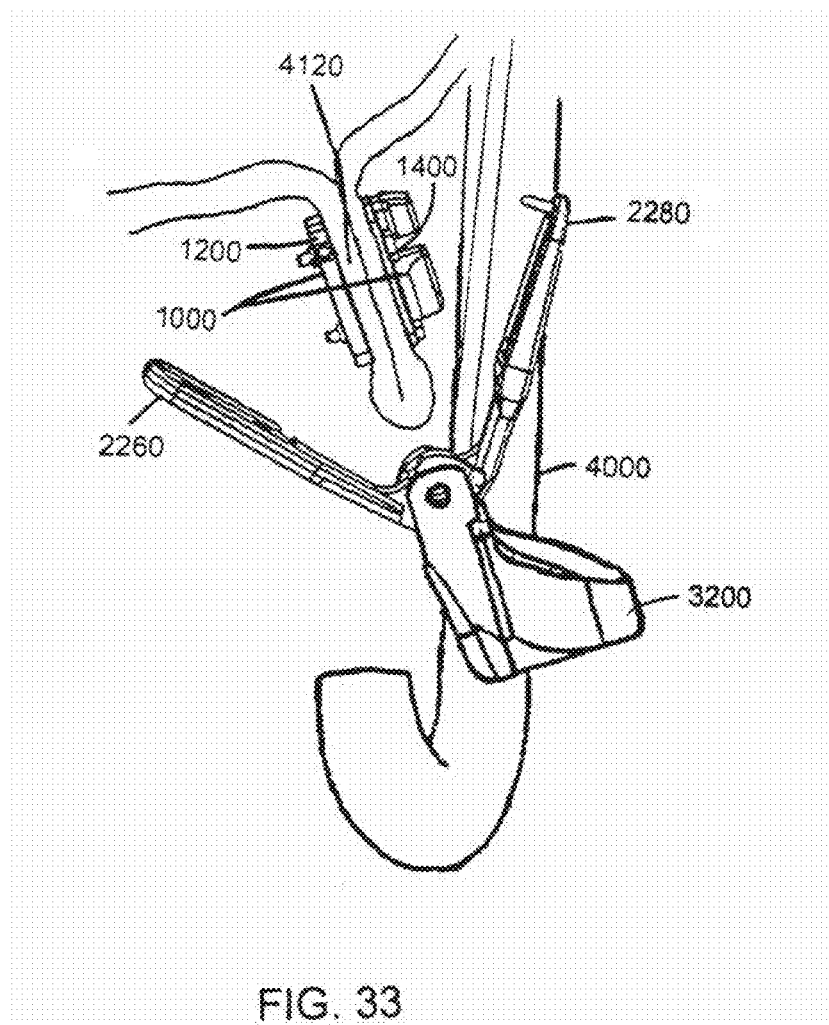
FIG. 33 is a fragmentary, perspective side view shown with the jaws of the plication device opened around the target tissue and the fastener plicating the target tissue.

Referring to FIG. 33, if the plication 4120 appears satisfactory, the proximal actuation handle is operated to lock the male and female parts 1200, 1400 of the fastener 1000 and release the coupled fastener 1000 from the jaws 2260, 2280. If the plication or fastener position is not satisfactory, prior to locking and release, the jaws 2260, 2280 can be opened, reoriented if necessary, and another plication 4120 can be formed.

After the fastener 1000 is applied, the jaws 2260, 2280 are, then, closed, the endoscope 4000 is straightened, and the end effector 2020 is re-docked over the distal end of the endoscope 4000. The clip implantation instrument and the endoscope 4000 are, together, withdrawn through the esophagus 4140 and out of the patient. Alternatively, the endoscope 4000 may be withdrawn first, followed by the withdrawal of the clip implantation instrument, preferably, under visualization with the endoscope.

Figure 34:
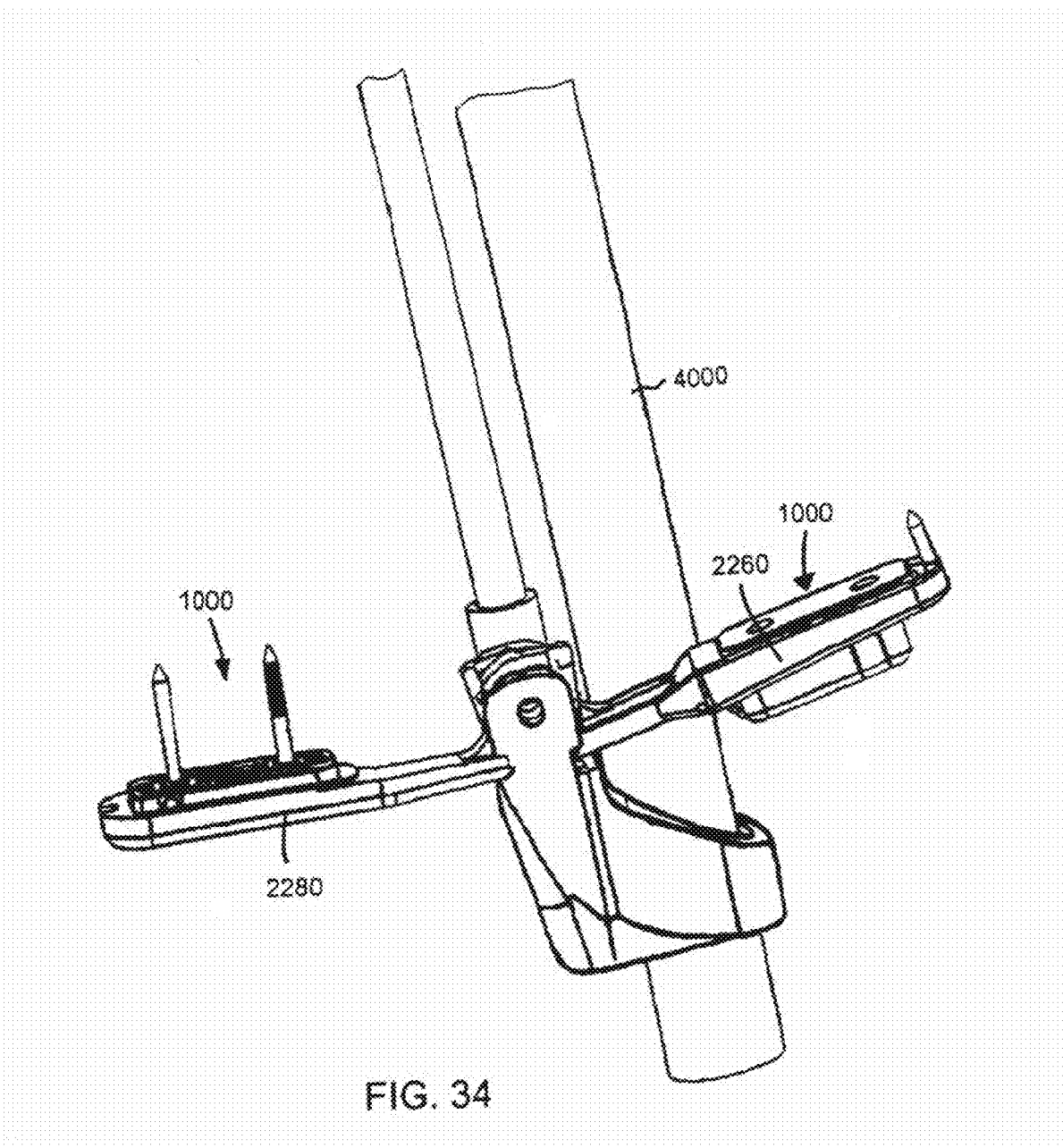
FIG. 34 is a fragmentary, perspective side view shown with the jaws of the plication device in an open position and the fastener disposed therein.

While it is preferable to decouple the clip implantation instrument from the endoscope 4000 during the procedure, it is appreciated that the clip implantation instrument may be operated while coupled to the endoscope. That is, referring to FIG. 34, the target tissue is approached by opening the jaws 2260, 2280 and simply retracting the end effector 2020 along the endoscope 4000 until the tissue 4100 about the LES 4020 is contacted. The jaws 2260, 2280 are, then, closed and the fastener 1000 applied, as described above. In order to utilize this procedure, the sleeve 3200 of the clip implantation instrument should be offset relative to the jaws 2260, 2280 so that the jaws 2260, 2280 can clear the endoscope 4000 when opening and closing.

While the clip implantation instrument has been shown adapted to be coupled to an endoscope, it is recognized that the clip implantation instrument may be modified for use in a manner in which it is always decoupled from an endoscope 4000.

Referring now to FIGS. 38 to 45, a second alternate embodiment of the distal end effector 7020 of the clip implantation instrument 200 is shown. The housing 7900 of the end effector 7020 is provided with a tapered nosepiece 8200 defining a longitudinal passage 8220 sized to receive a guidewire 8240. The guidewire 8240 may have a diameter less than one millimeter. Preferably, the nosepiece 8200 is formed from a highly flexible material such as silicone.

Figure 35:
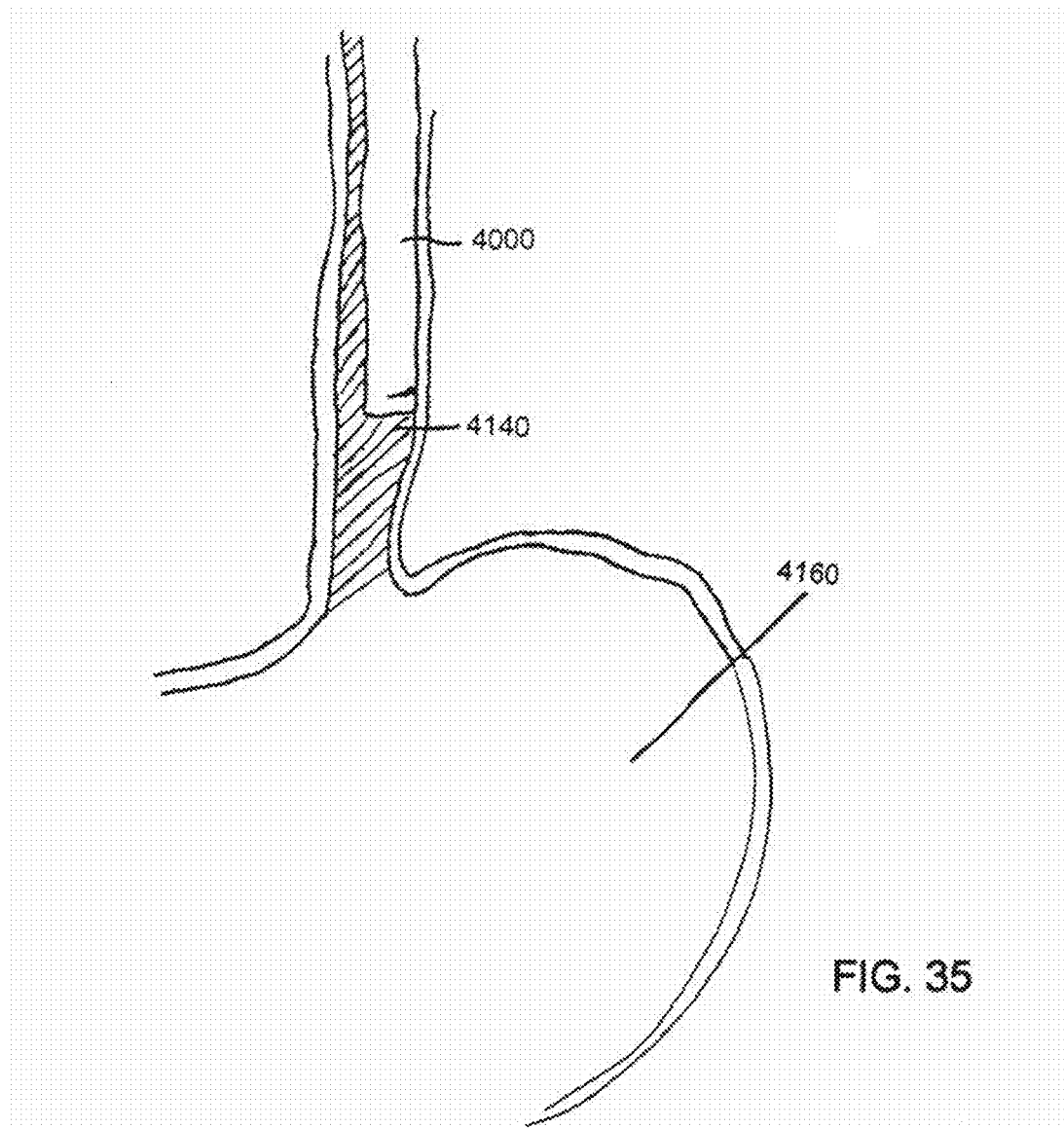
FIGS. 35 through 45 are fragmentary partially cross-sectional and partially elevational views illustrating the procedure according to the invention in which the retractor is advanced through a working channel of an endoscope into the stomach and operated under view of the endoscope.
Figure 36:
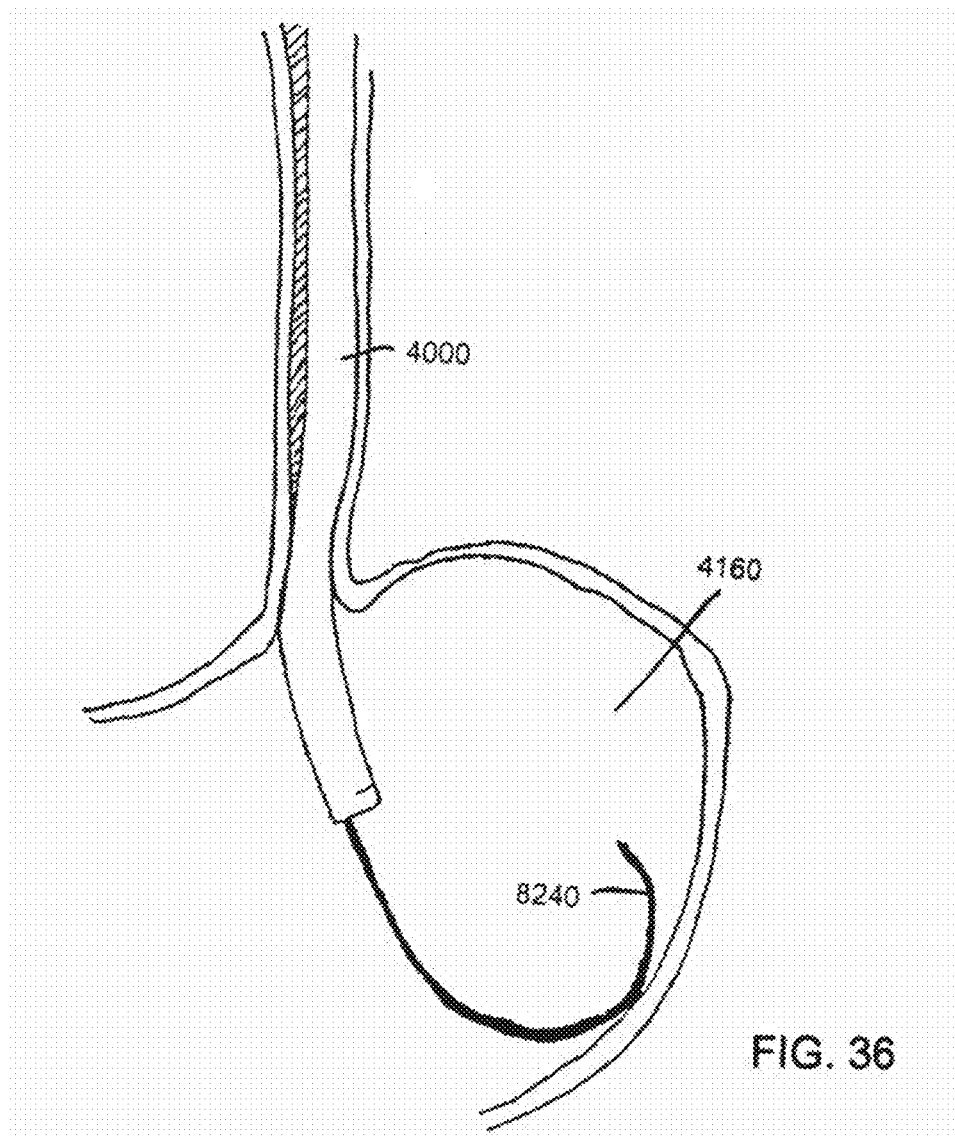
Figure 37:
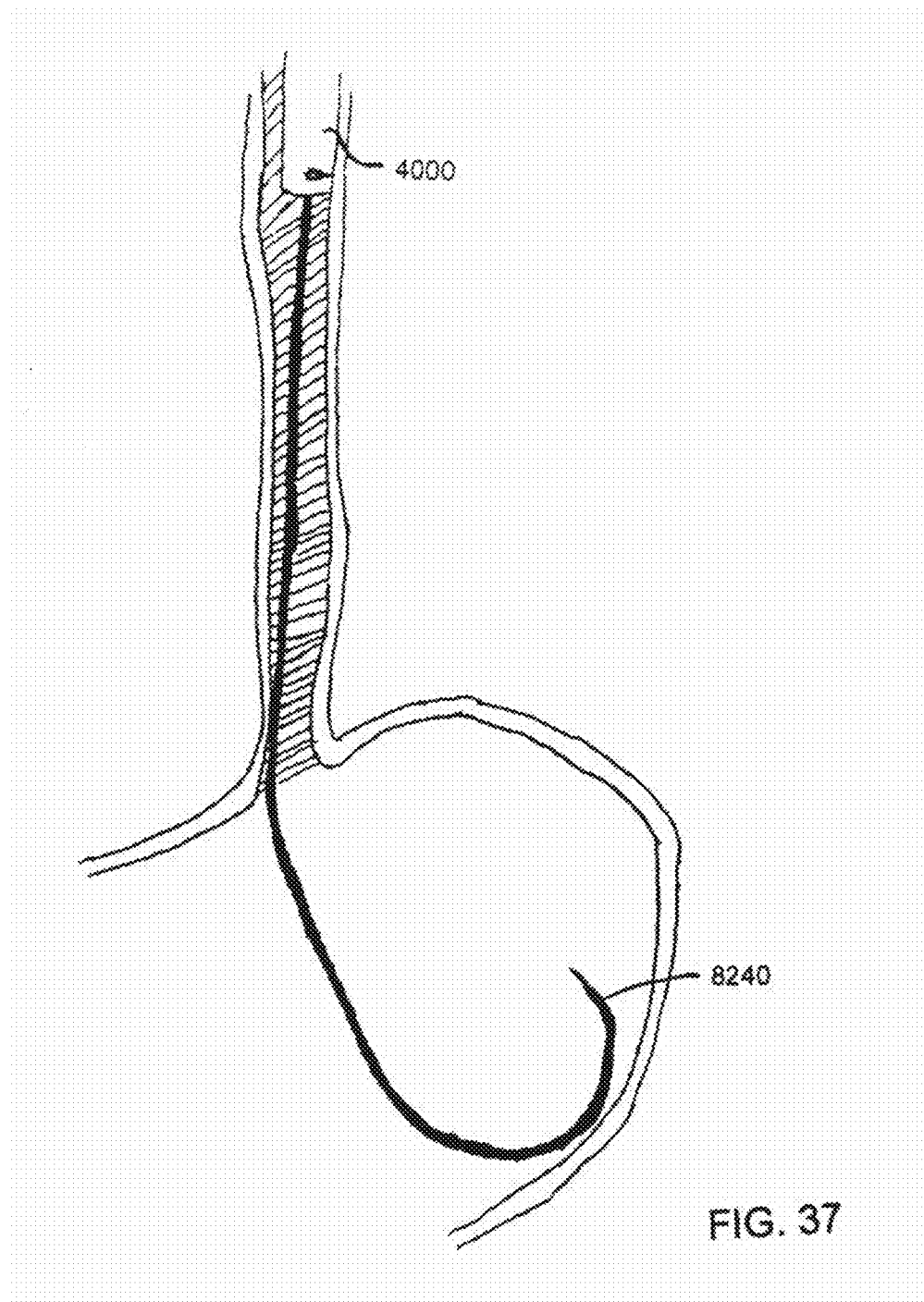
Figure 38:
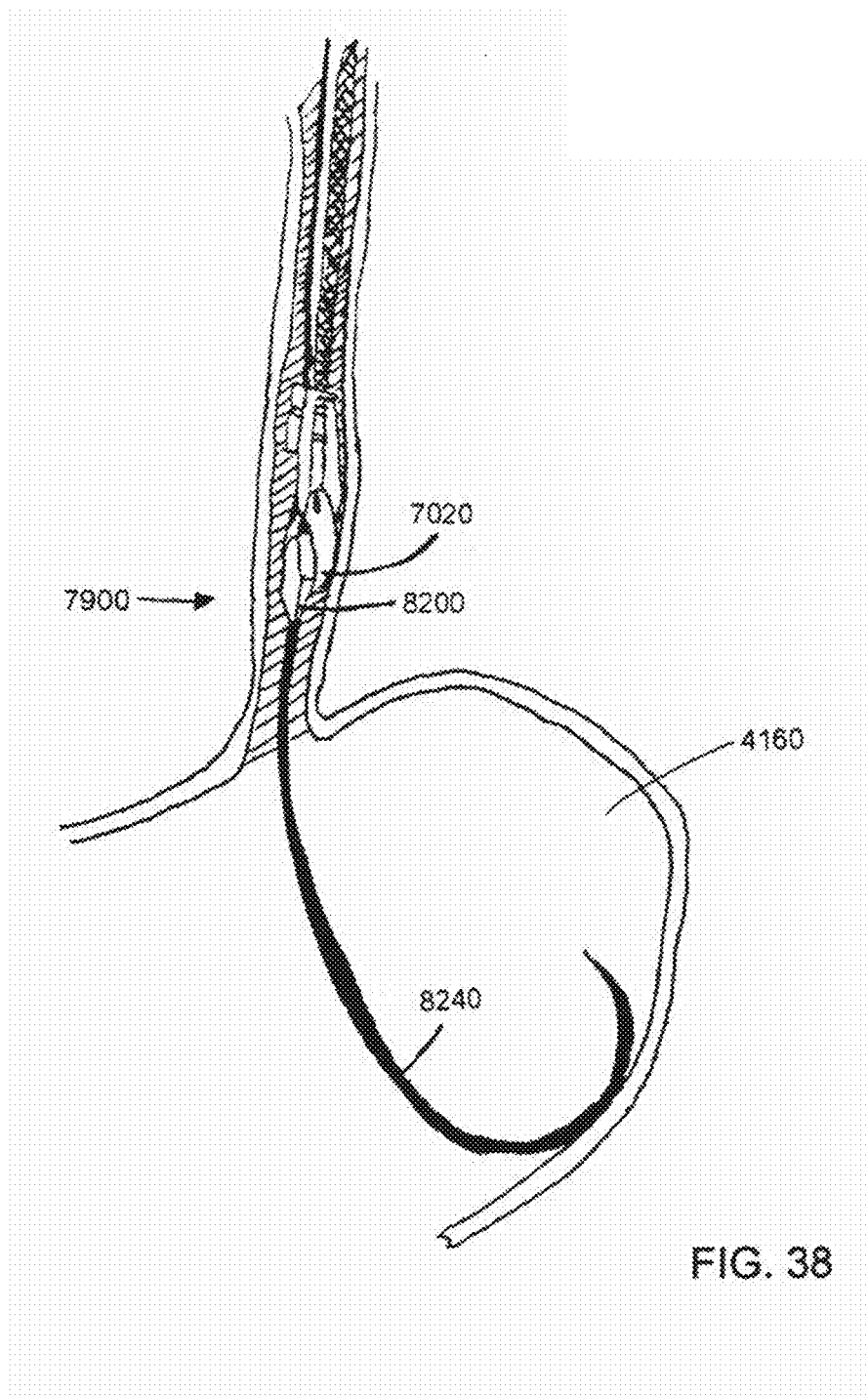
Figure 39:
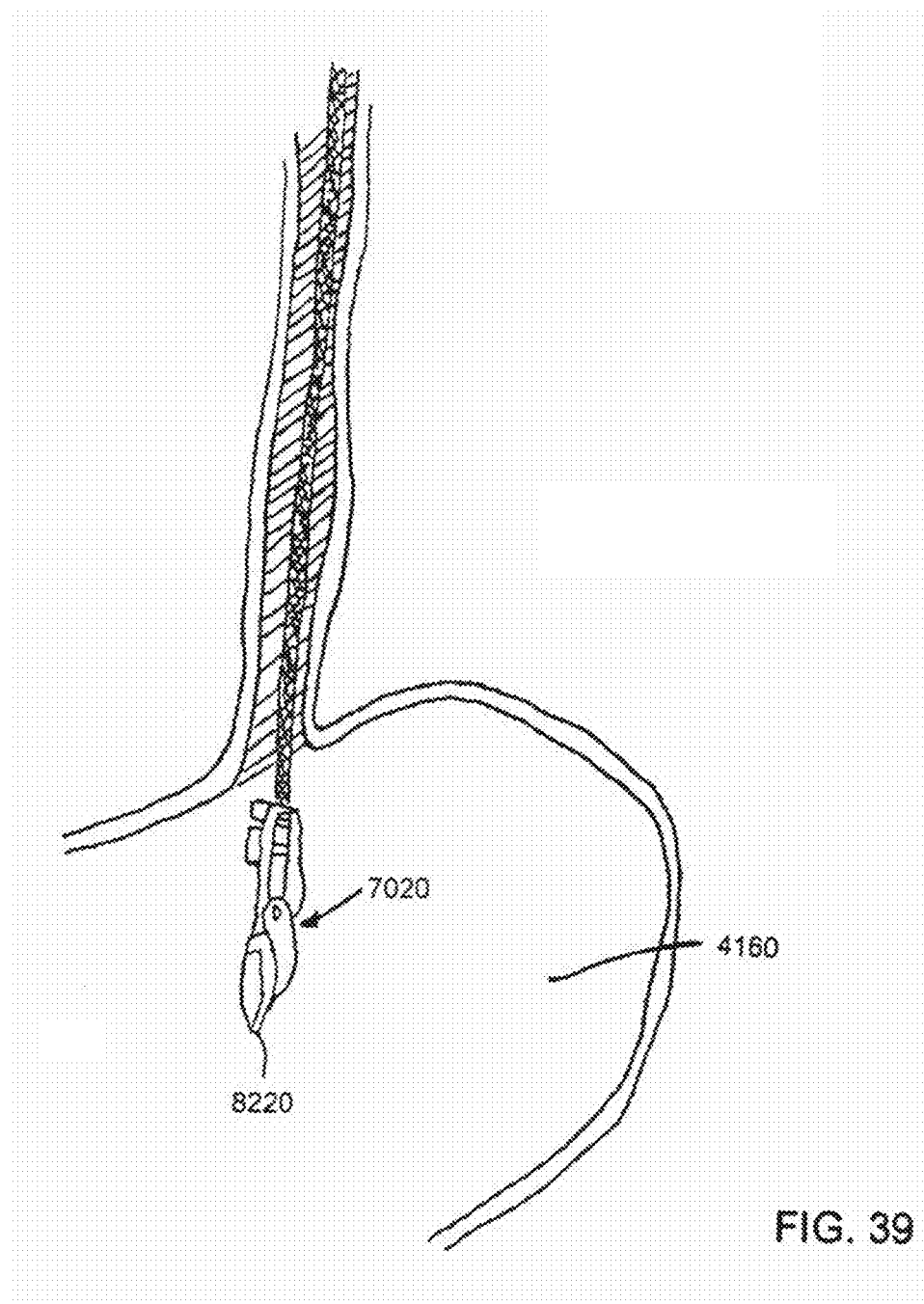
Figure 40:
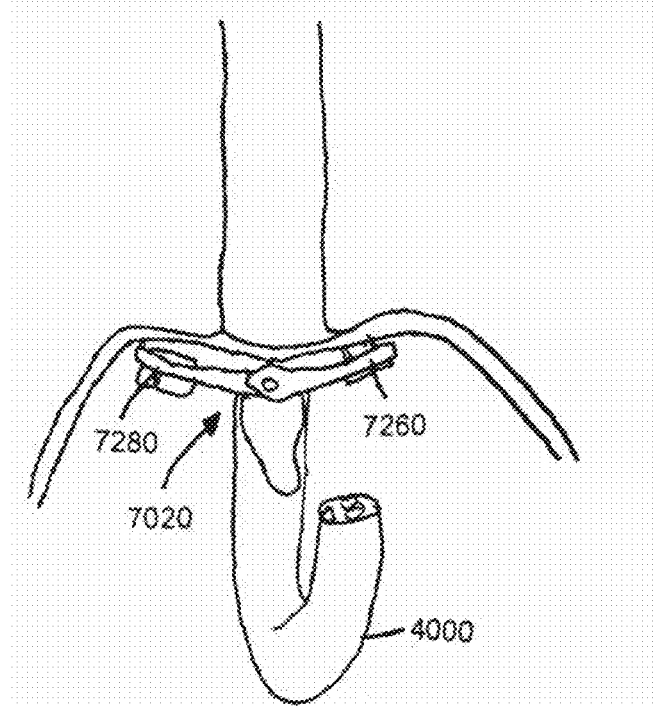
Figure 41:
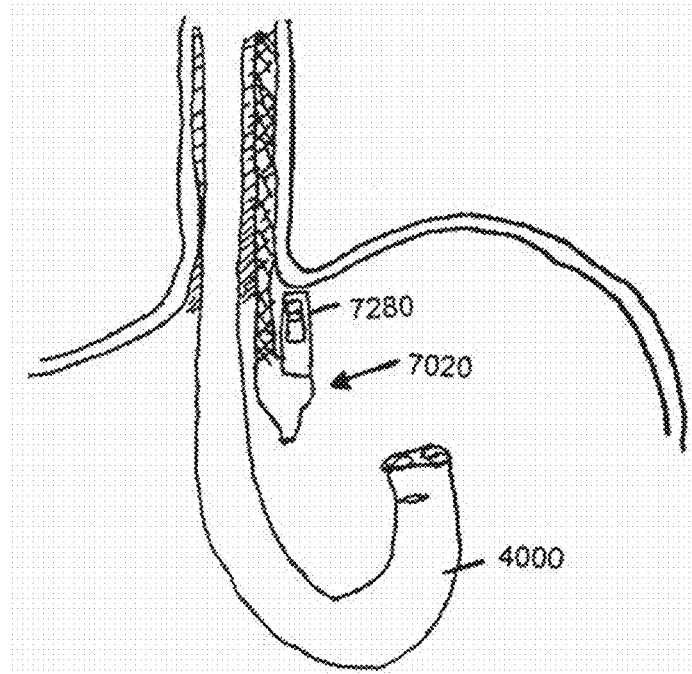
Figure 42:
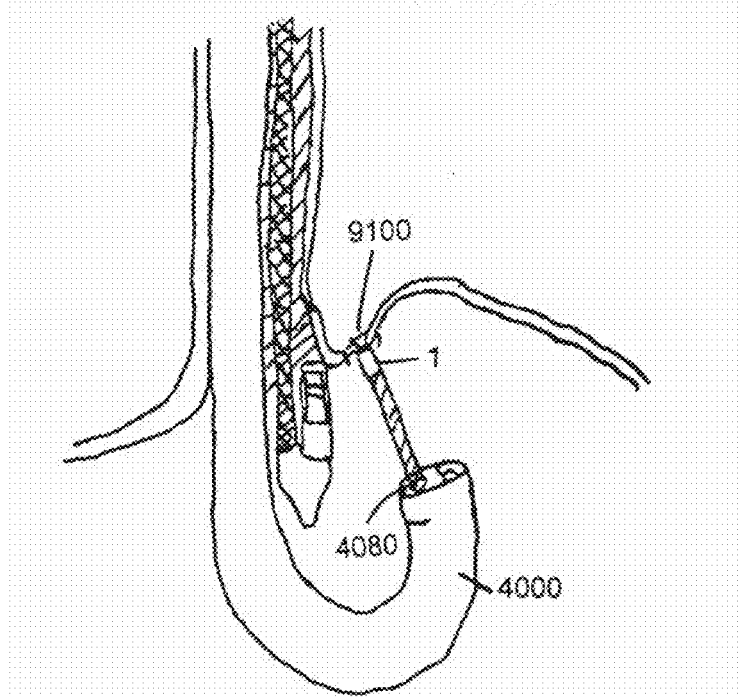
Figure 43:
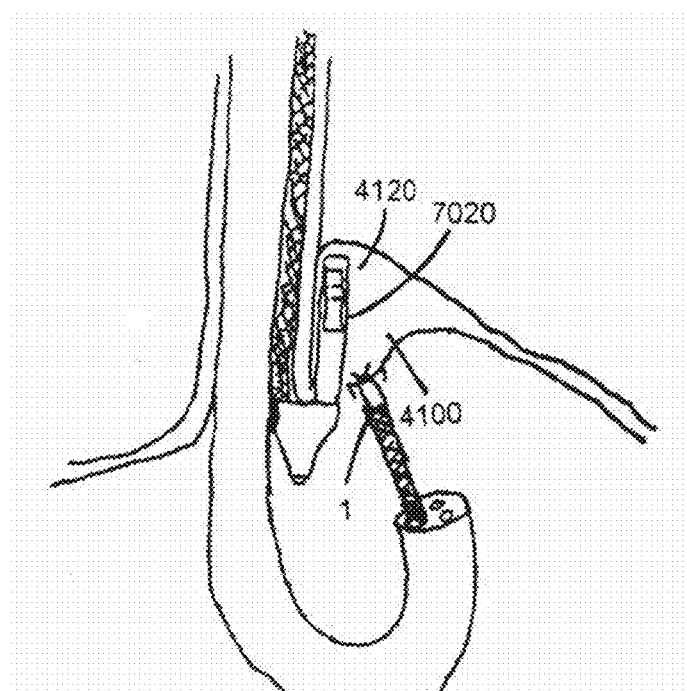
Figure 44:
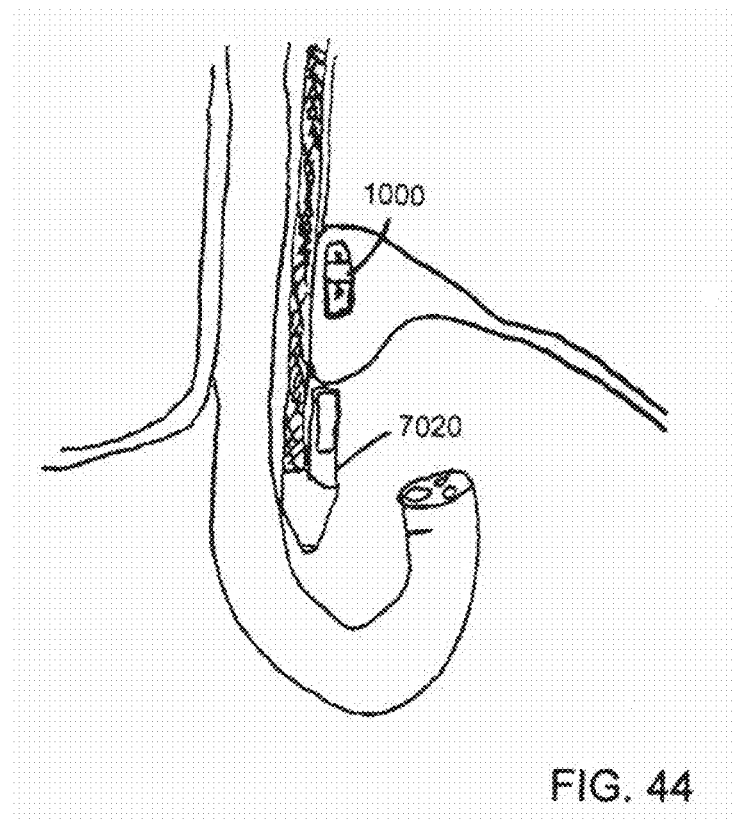
Figure 45:
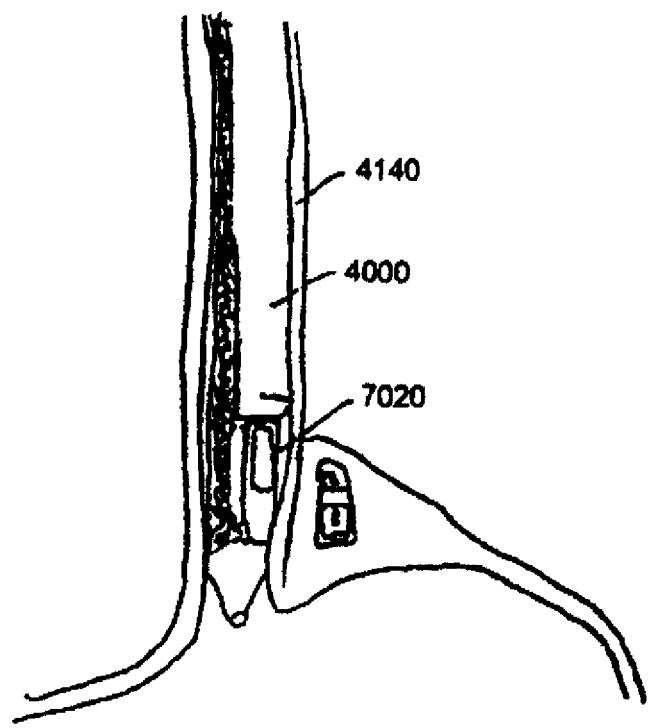

According to a preferred method of use, referring to FIG. 35, an endoscope 4000 is, preferably, first inserted through the tracheopharangeal passage 4140 and into the stomach 4160 in accord with a well-known procedure. Next, referring to FIG. 36, a guidewire 8240 is advanced through the endoscope into the stomach 4160. Referring to FIG. 37, the endoscope 4000 is, then, preferably withdrawn from over the guidewire 8240. Referring to FIG. 38, the end effector 7020 is, then, blindly advanced over the guidewire 8240 and introduced into the stomach 4160. The tapered nosepiece 8200 and relatively small head-on cross-sectional area of the system facilitate the introduction. Referring to FIG. 39, after the end effector 7020 is located in the stomach 4160, the guidewire 8240 is, preferably, withdrawn from the stomach 4160. Referring now to FIGS. 40 and 41, the endoscope 4000 is, then, reintroduced alongside the control shaft 2060 of the clip implantation instrument, advanced into the stomach 4160, and retroflexed to view the end effector 7020. The jaws 7260, 7280 of the end effector 7020 are, also, opened and brought adjacent the tissue that is to be plicated. Referring to FIG. 42, the retractor 1 is deployed through a working channel 4080 of the endoscope 4000 and operated to engage tissue 9100 at a location at which the fold of a plication 4120 is desired. As set forth above, the needles 4 of the retractor 1 extend through the mucosa 202 and the muscularis 204 (deep muscle) to, thereby, hold these layers together and prevent delamination. Turning to FIG. 43, the jaws of the end effector 7020 are closed, forming a plication 4120 about the engaged tissue 4100, the plication 4120 being substantially parallel to the esophagus 4140. The plication 4120 extends from the location held by the retractor 1 to the end of the jaws 7260, 7280 of the clip implantation instrument. Referring to FIG. 44, the fastener 1000 is deployed and the jaws 7260, 7280 of the end effector 7020 are opened. Referring to FIG. 45, the jaws 7260, 7280 of the end effector 7020 are closed, and the end effector 7020 is withdrawn through the esophagus 4140 under visualization of the endoscope 4000. That is, the closed jaws of the end effector 7020 are, preferably, positioned directly distal of the endoscope 4000 to minimize the cross-sectional area of the endoscope/clip implantation instrument system as well as to permit constant visualization of the end effector during the retraction of the end effector through the esophagus 4140.

A common procedure during flexible endoscopy is the exchange of an endoscope during a procedure. If the first endoscope 4000 is in a position within the alimentary tract that was difficult to achieve, and it is desired that the second (exchange) endoscope be in the same position, the tissue retractor 1 could be used to guide the second scope into the position of the first scope. A flexible endoscopic version of the retractor 1 according to the present invention can be provided with a removable handle 100. Therefore, when a scope exchange is necessary, the tissue retractor 1 can be passed through the first scope and deployed in the tissue at the desired location as shown, for example, in FIGS. 31, 42, and 43. The handle 100 can, then, be removed. The first scope 4000 can, then, be slid over the tissue retractor shaft 8 and removed, leaving the retractor shaft 8 in place. Then, the second scope can be fed over the tissue retractor shaft 8, much like the guidewire 8240 used in FIGS. 36, 37, and 38, and the second scope advanced to the original position. Thereafter, the shaft 8 can be released and removed when desired.

Other embodiments of the invention will be apparent to those skilled in the art from consideration of the specification and practice of the invention disclosed herein. It is intended that the specification and examples be considered as exemplary only.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

There have been described and illustrated herein several embodiments of retractors and methods for the endoluminal treatment of Gastroesophageal Reflux Disease (GERD). While particular embodiments of the invention have been described, it is not intended that the invention be limited thereto, as it is intended that the invention be as broad in scope as the art will allow and that the specification be read likewise. For example, while particular preferred dimensions have been provided for the retractor, it is appreciated that the system and its elements may have different relative sizes. For example, the cross-sectional areas can be decreased further if a pediatric endoscope (4 to 6 mm) is used. Also, while a "looking back" clip implantation instrument has been disclosed particularly for fastener application designed to treat GERD, it is appreciated that a "forward looking" straight instrument with similar jaw assembly can be used to apply the fastener for treatments of other conditions, e.g., obesity, ulceration, stomach cancer, implantation of pH measurement or monitoring devices, feeding tubes, etc. Moreover, a straight device can be smaller in diameter and be operated through a working channel of an endoscope. It will, therefore, be appreciated by those skilled in the art that yet other modifications could be made to the provided invention without deviating from its spirit and scope as so claimed.

We claim:

1. A retractor for manipulating an object, comprising:
   a body having a proximal end and a distal end;
   a retraction device having:
      a head connected to said distal end of said body, said head comprising a curved track having a first portion and a second portion;
      a connector movably disposed in said body;
      flexible needles of a shape memory material having a memory shape, said needles connected to said connector and each having a distal tip, said memory shape of said needles including a portion with an arcuate shape biasing said needles in a memory direction out and away from said head and toward the proximal end of said body to position said distal tip of each of said needles closer to said body when said needles are fully extended out of said head than when said needles are only partially extended out of said head, each of said flexible needles slidably disposed within a respective portion of said curved track; and
      a shim separating said flexible needles from each other while in said respective portion of said curved track; and
   an actuation device connected to said proximal end of said body and operatively connected to said connector through said body, said actuation device, upon actuation thereof, moving said connector to selectively extend said needles out of said head in different directions and withdraw said needles into said head.

2. The retractor according to claim 1, wherein:
   said head comprises:
      a first tip half defining at least the first portion of the curved track; and
      a second tip half defining at least the second portion of the curved track.

3. The retractor according to claim 2, wherein the shim is disposed between said first tip half and said second tip half, said two tip halves and said shim defining said curved tracks.

4. The retractor according to claim 2, wherein said tracks have track exits open to the environment.

5. The retractor according to claim 2, wherein said tracks have a shape corresponding to said memory shape of a portion of said needles.

6. The retractor according to claim 1, wherein said memory shape of said needles includes a substantially linear proximal portion and an arcuate distal portion.

7. The retractor according to claim 1, wherein:
   said body has a longitudinal extent defining a longitudinal direction; and
   said needles extend out of said head in a direction substantially orthogonal to said longitudinal direction.

8. The retractor according to claim 1, wherein said head has an anchoring spike retaining said head at a user-selected placement position.

9. The retractor according to claim 1, wherein said actuation device has an overstroke preventor connected to said needles and operable to limit an extension distance of said needles out of said head.

10. The retractor according to claim 1, further comprising a proximal stop disposed in said body and limiting a retraction range of said needles.

11. In combination with a flexible endoscope having at least one working channel, a tissue retractor for manipulating tissue inside a patient, the tissue retractor comprising:
   a body having a proximal end and a distal end;
   a retraction device having:
      a head connected to said distal end of said body, said head comprising a curved track having a first portion and a second portion;
      a connector movably disposed in said body; and
      flexible needles of a shape memory material having a memory shape, said needles connected to said connector and each having a distal tip, said memory shape of said needles including a portion with an arcuate shape biasing said needles in a memory direction out and away from said head and toward the proximal end of said body to position said distal tip of each of said needles closer to said body when said needles are fully extended out of said head than when said needles are only partially extended out of said head, each of said flexible needles slidably disposed within a respective portion of said curved track; and
      a shim separating said flexible needles from each other while in said respective portion of said curved track; and
   an actuation device connected to said proximal end of said body and operatively connected to said connector through said body, said actuation device, upon actuation thereof, moving said connector to selectively extend said needles out of said head in different directions and withdraw said needles into said head; and
   said body and said retraction device are sized to fit within the working channel of the endoscope.

12. The retractor according to claim 11, wherein said needles are sized to selectively grasp alimentary tract tissue.

13. The retractor according to claim 11, wherein:
   said head comprises:
      a first tip half defining at least the first portion of the curved track; and
      a second tip half defining at least the second portion of the curved track.

14. The retractor according to claim 13, wherein the shim is disposed between said first tip half and said second tip half, said two tip halves and said shim defining said curved tracks.

15. The retractor according to claim 13, wherein said tracks have track exits open to the environment.

16. The retractor according to claim 13, wherein said tracks have a shape corresponding to said memory shape of a portion of said needles.

17. The retractor according to claim 11, wherein said memory shape of said needles includes a substantially linear proximal portion and an arcuate distal portion.

18. The retractor according to claim 11, wherein:
said body has a longitudinal extent defining a longitudinal direction; and
said needles extend out of said head in a direction substantially orthogonal to said longitudinal direction.

19. The retractor according to claim 11, wherein said head has an anchoring spike retaining said head at a user-selected placement position.

20. A retractor for manipulating an object, comprising:
a body having a proximal end and a distal end;
a retraction device having:
 a head connected to said distal end of said body, said head comprising a curved track having a first portion and a second portion;
 flexible needles of a shape memory material having a memory shape, each of said flexible needles slidably disposed within a respective portion of said curved track, said needles:
  movably disposed in said body; and
  each having a distal tip, said memory shape of said needles including a portion with an arcuate shape biasing said needles in a memory direction out and away from said head and toward the proximal end of said body to position said distal tip of each of said needles closer to said body when said needles are fully extended out of said head than when said needles are only partially extended out of said head; and
 a shim separating said flexible needles from each other while in said respective portion of said curved track; and
an actuation device connected to said proximal end of said body and operatively connected to said needles through said body, said actuation device, upon actuation thereof, moving said needles to selectively:
 extend said needles out of said head in different directions; and
 withdraw said needles into said head; and
said body and said retraction device are sized to fit within a working channel of an endoscope.

* * * * *